United States Patent [19]
Andino et al.

[11] Patent Number: 5,637,074
[45] Date of Patent: Jun. 10, 1997

[54] APPARATUS AND METHOD FOR IMPLANTING PROSTHESES WITHIN PERIURETHRAL TISSUES

[75] Inventors: Rafael V. Andino, Loganville; Joseph N. Genese, Covington; Ken Butcher, Conyers; David E. Cerny, Lilburn, all of Ga.; Christopher J. Brooks, Glen Head, N.Y.

[73] Assignee: C. R. Bard, Inc., Covington, Ga.

[21] Appl. No.: 305,869

[22] Filed: Sep. 14, 1994

Related U.S. Application Data

[63] Continuation-in-part of Ser. No. 120,943, Sep. 14, 1993, Pat. No. 5,437,603.
[51] Int. Cl.$^6$ ........................................................ A61F 2/00
[52] U.S. Cl. ........................................ 600/29; 128/DIG. 25
[58] Field of Search .................. 128/DIG. 25, DIG. 26; 600/29–32; 604/115–117, 174, 175

[56] References Cited

U.S. PATENT DOCUMENTS 3,016,899  1/1962  Stenvall ............................. 604/116
4,802,479  2/1989  Haber et al. ....................... 128/DIG. 25

*Primary Examiner*—Angela D. Sykes
*Assistant Examiner*—John P. Lacyk
*Attorney, Agent, or Firm*—Jones & Askew

[57] ABSTRACT

An apparatus is disclosed for guiding a medical instrument to a predetermined target location within the periurethral tissues of a patient. The apparatus directs the instrument along a predetermined path with respect to the patient's urethra and limits penetration of the instrument to a predetermined depth. The disclosed embodiment comprises an apparatus for implanting inflatable prostheses within the periurethral tissues to coapt the urethra and thereby manage incontinence.

A method for effecting coaptation of a urethra of a patient is also disclosed. According to this method, a pair of working channels are formed within the periurethral tissues, and an inflatable prosthesis is introduced into each working channel. The prostheses are inflated only after both working channels have been formed, and preferably after both prostheses have been positioned within their respective working channels. The inflated prostheses confront the urethra and effect coaptation of the urethra.

34 Claims, 29 Drawing Sheets

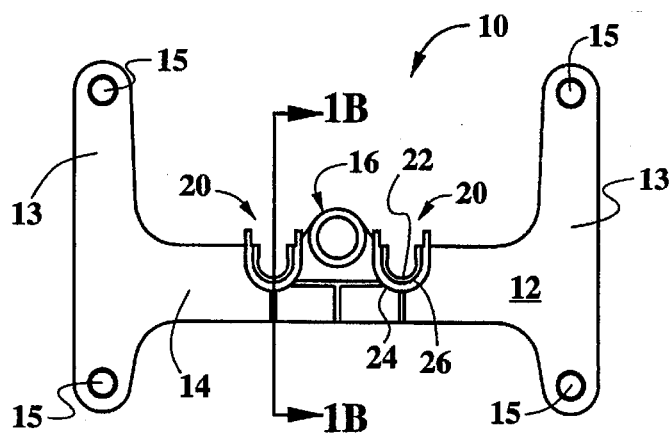
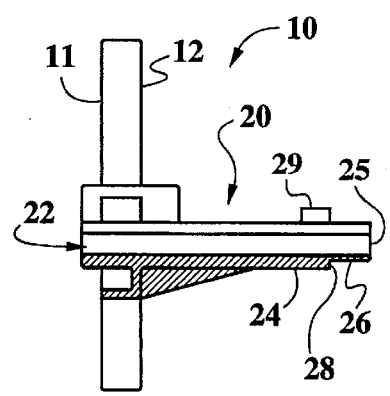
*Fig. 1A*  *Fig. 1B*
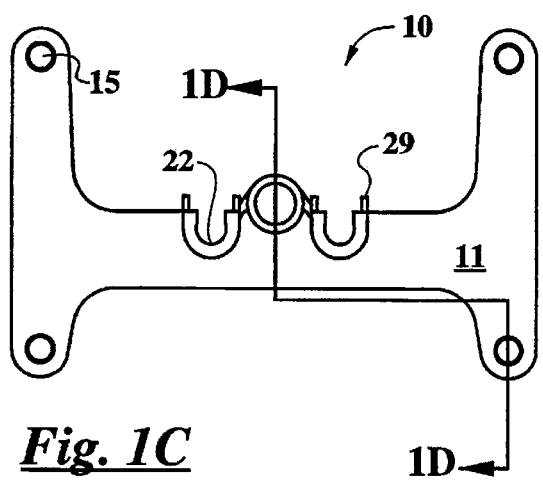
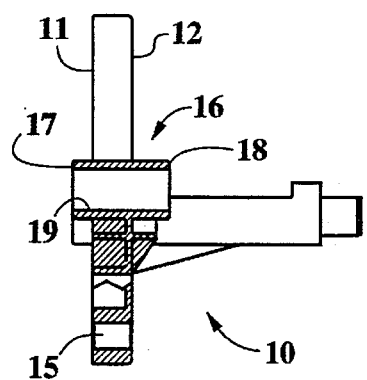
*Fig. 1C*  *Fig. 1D*
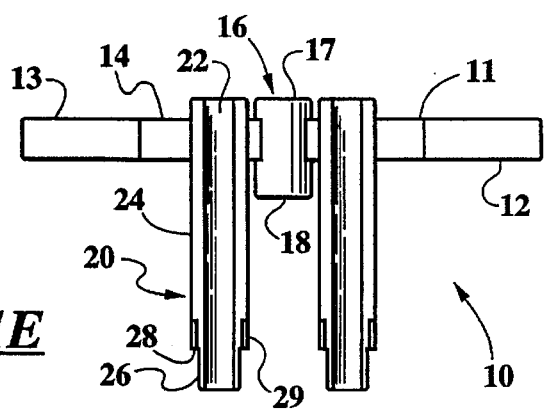
*Fig. 1E*

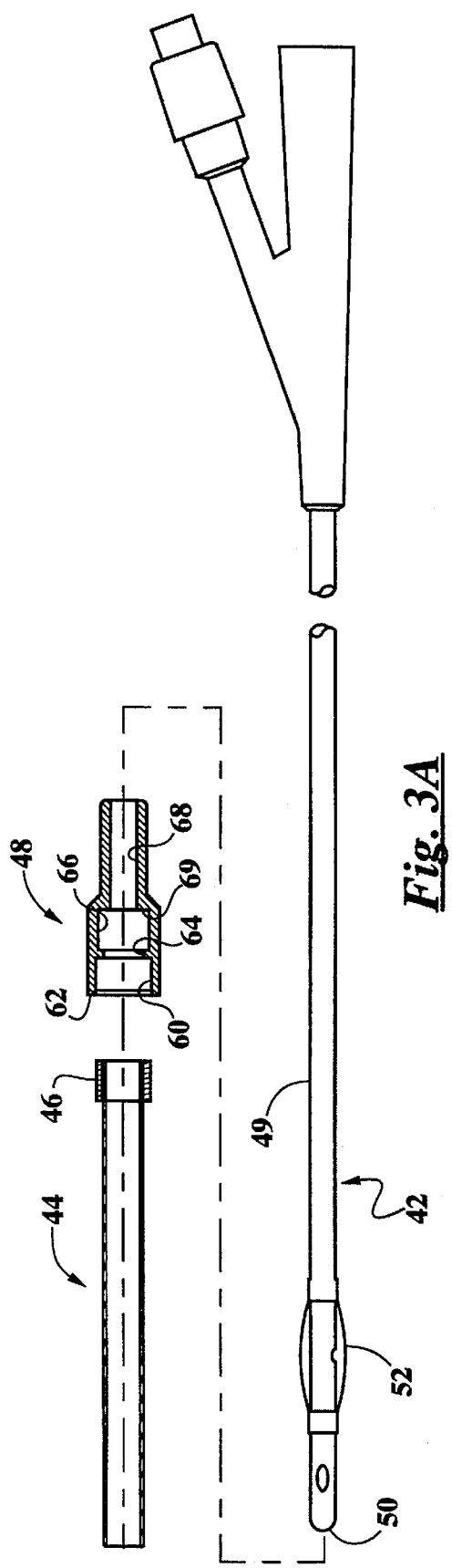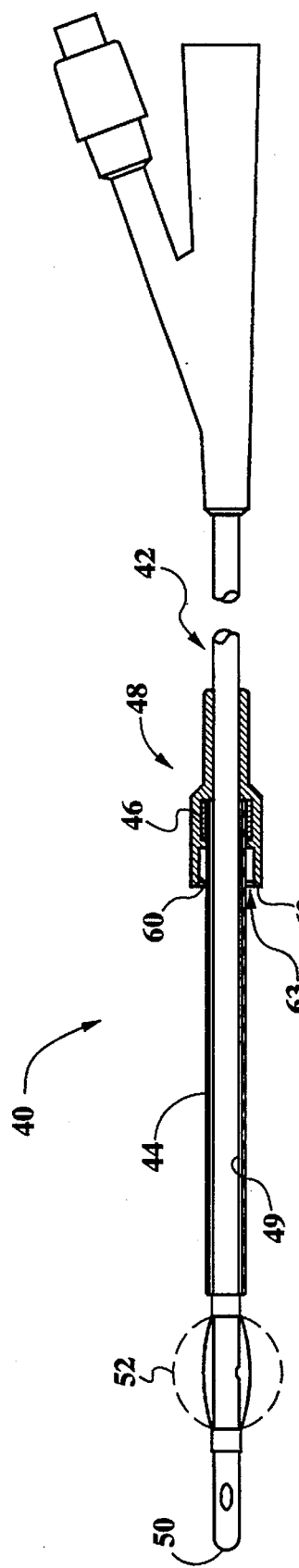

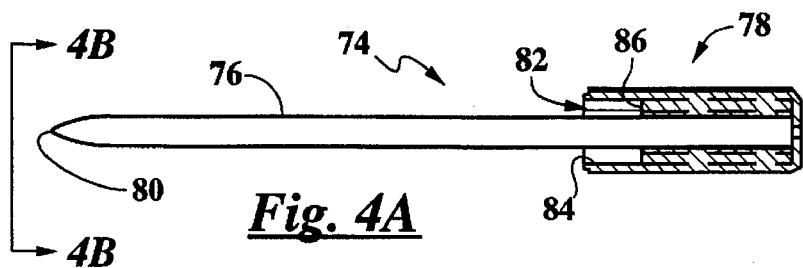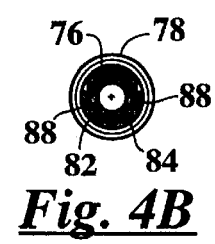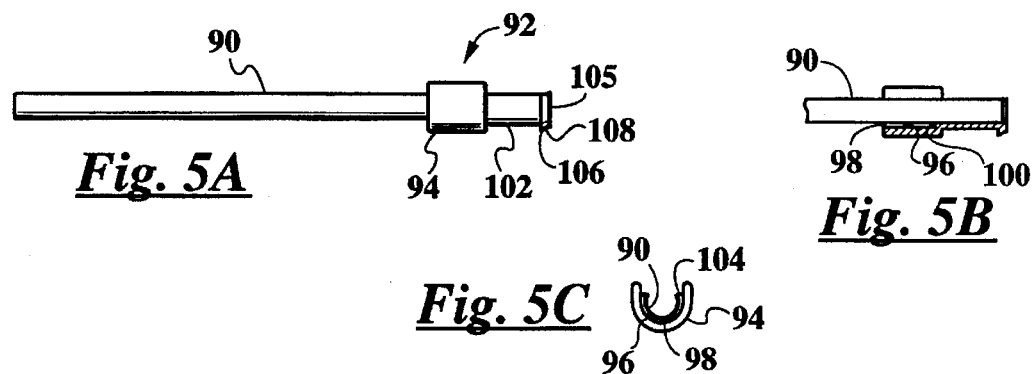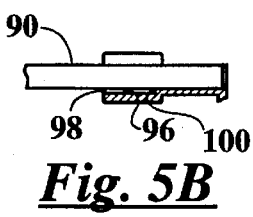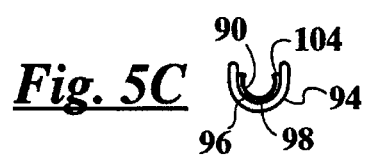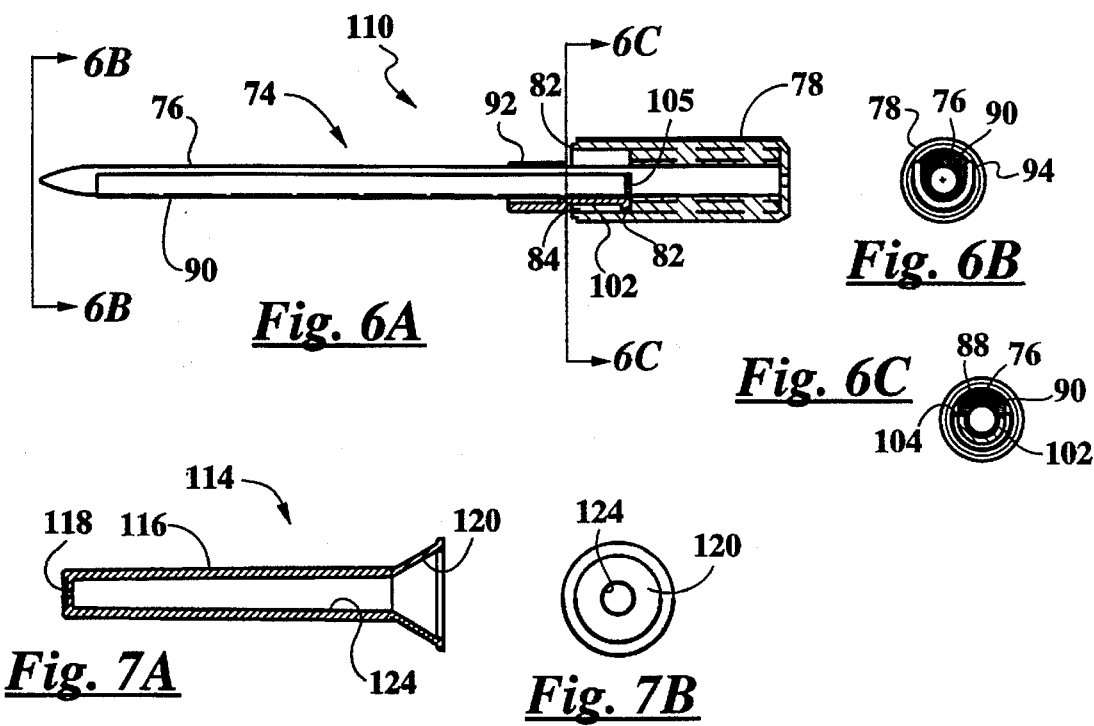

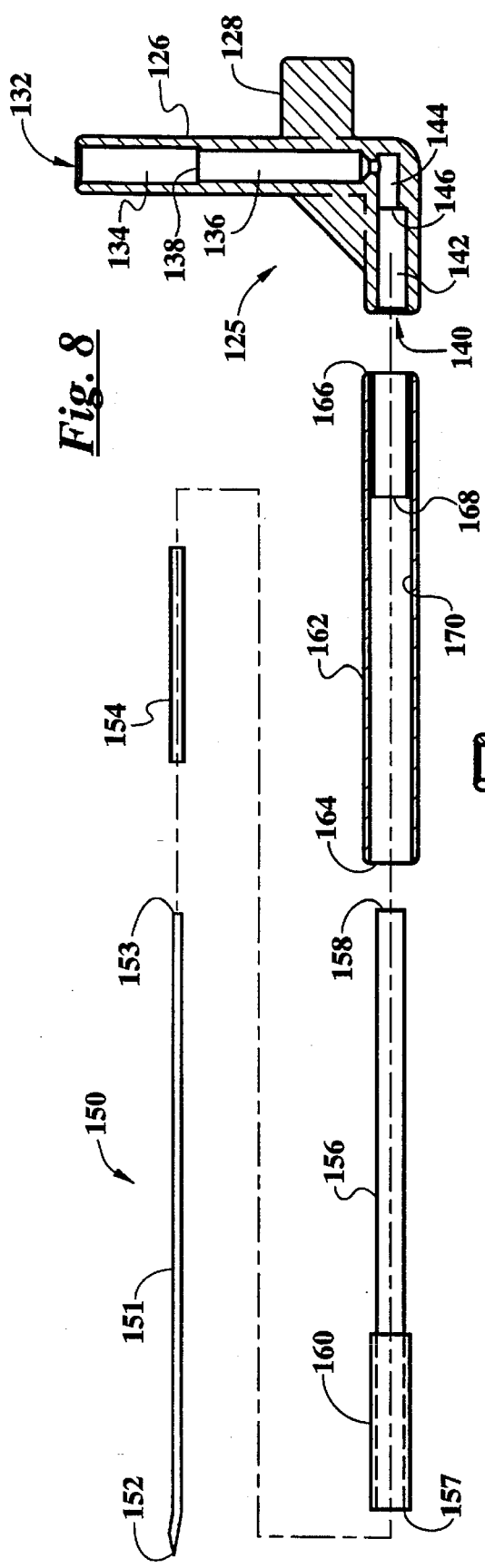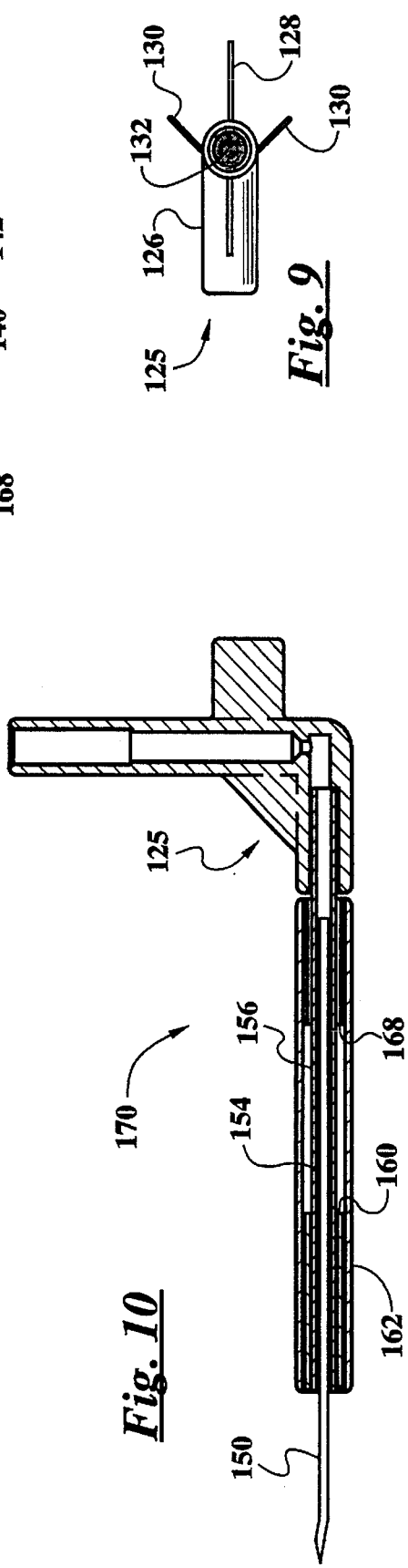

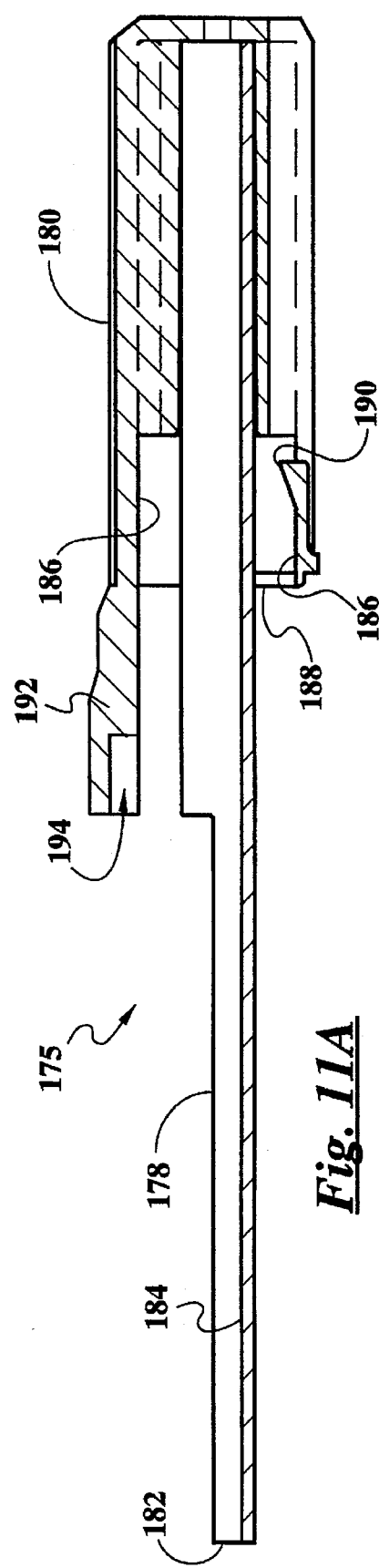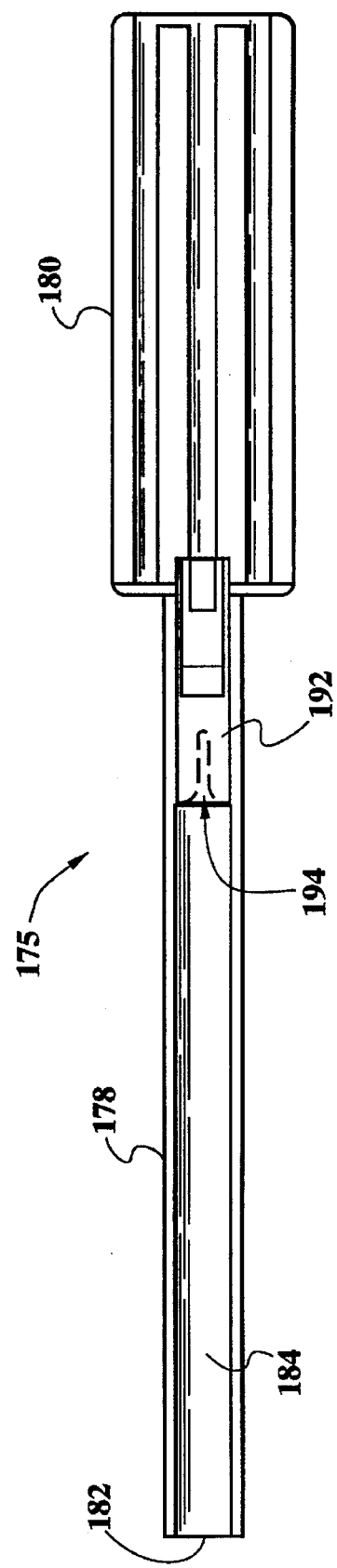

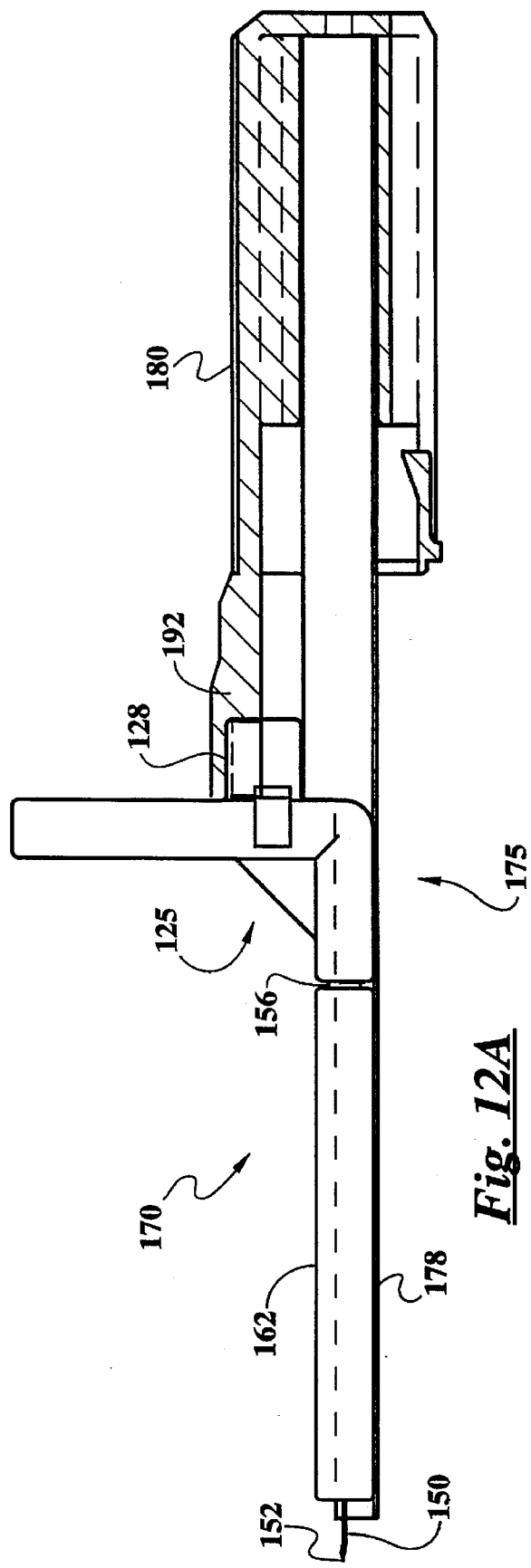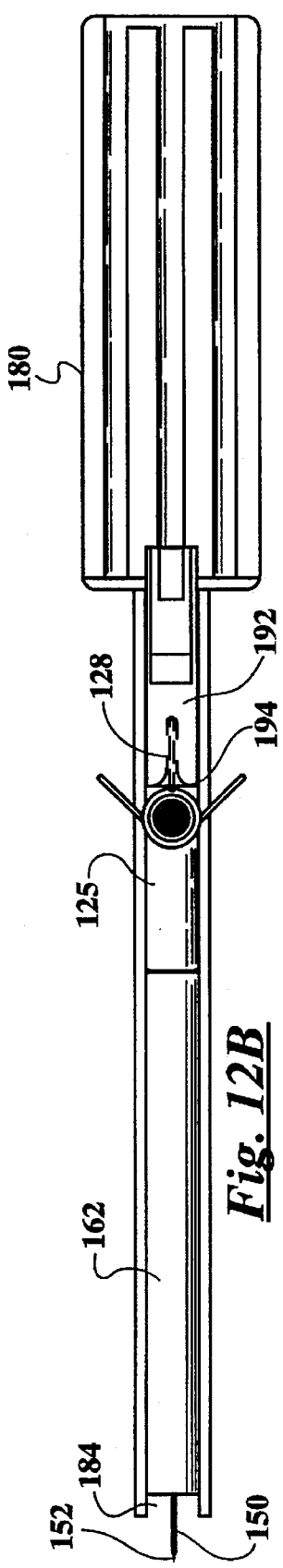
Fig. 12A
Fig. 12B

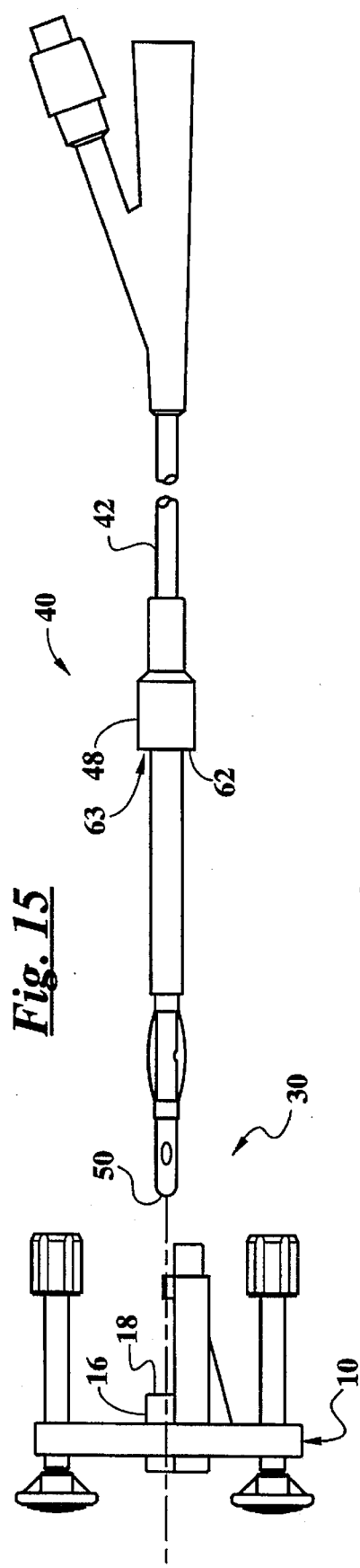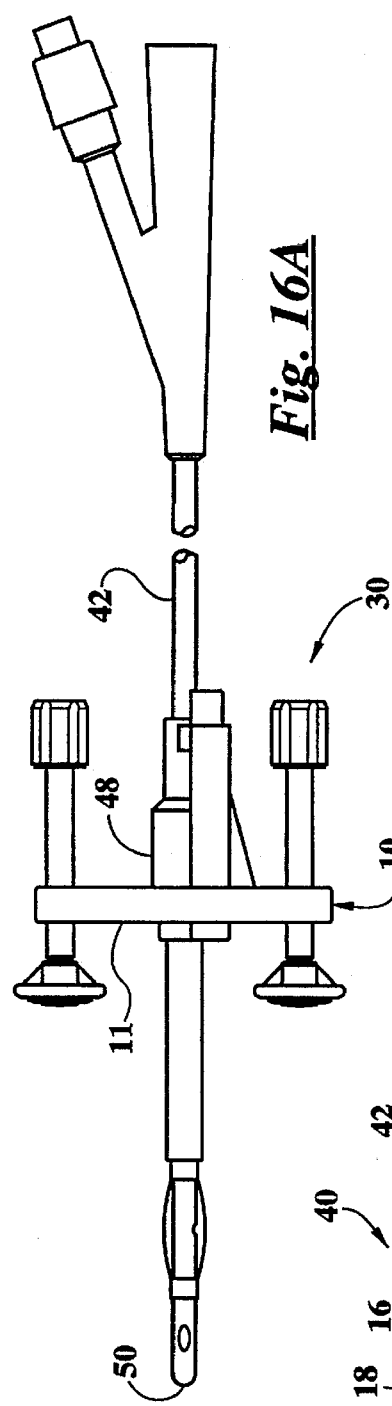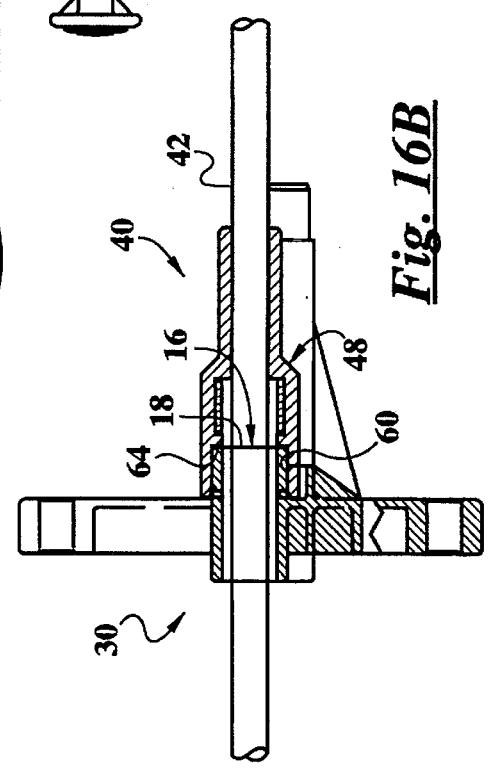

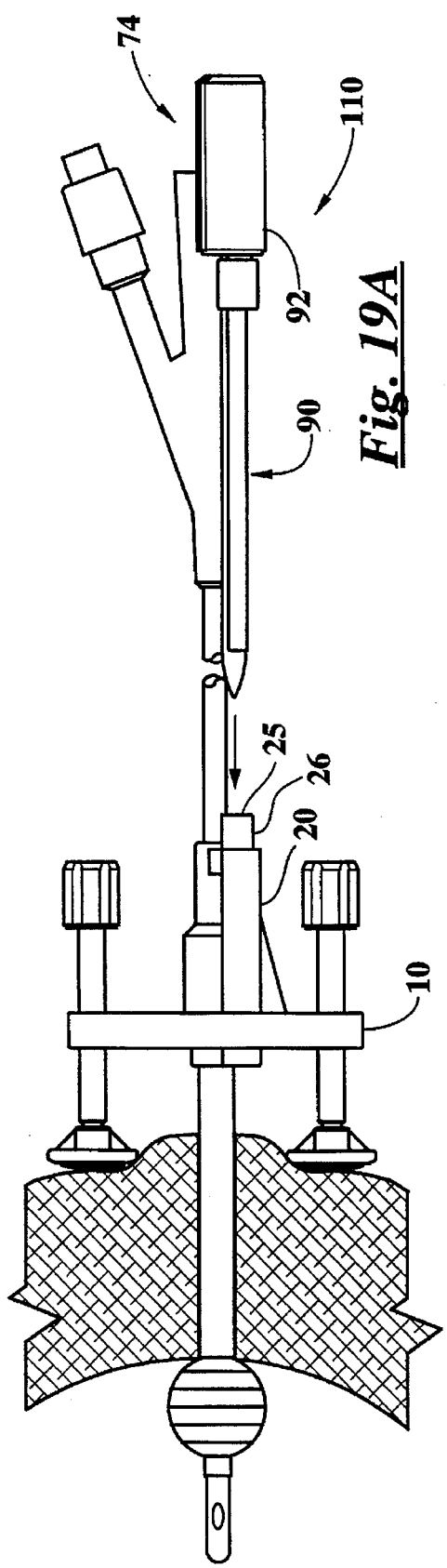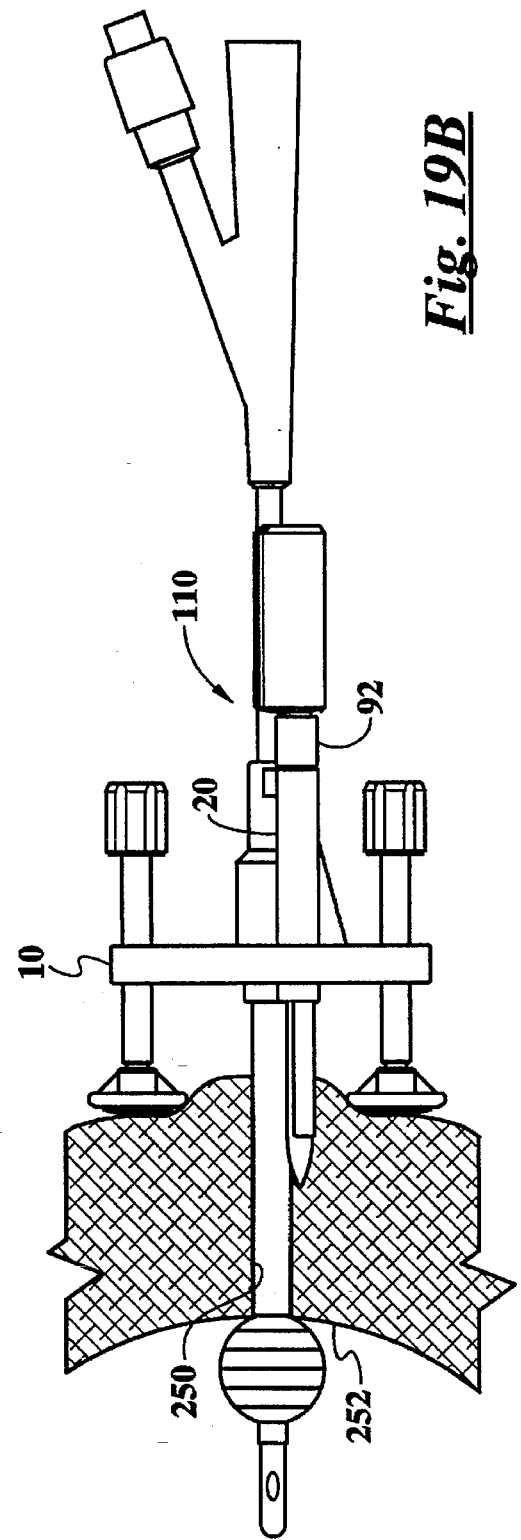

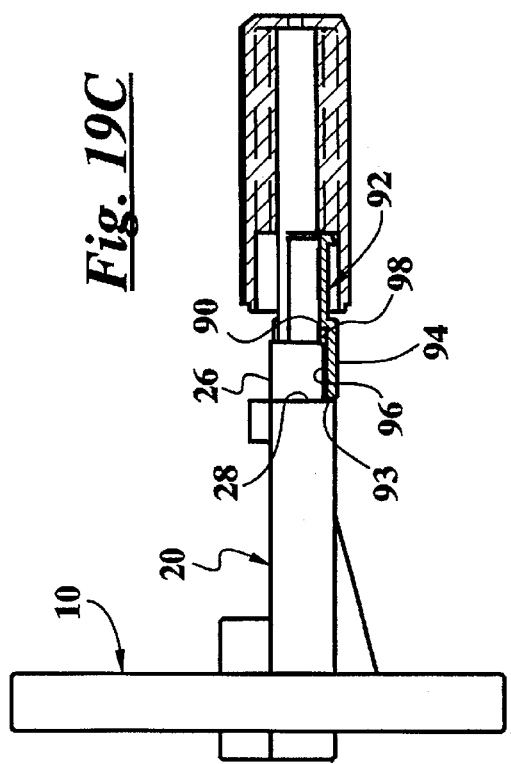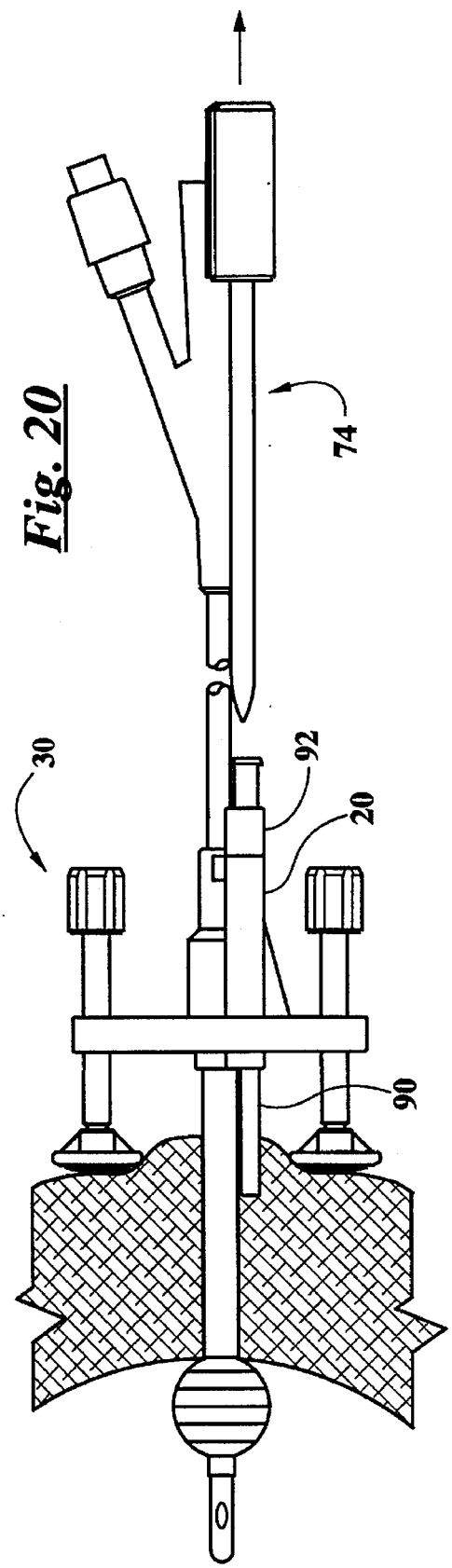

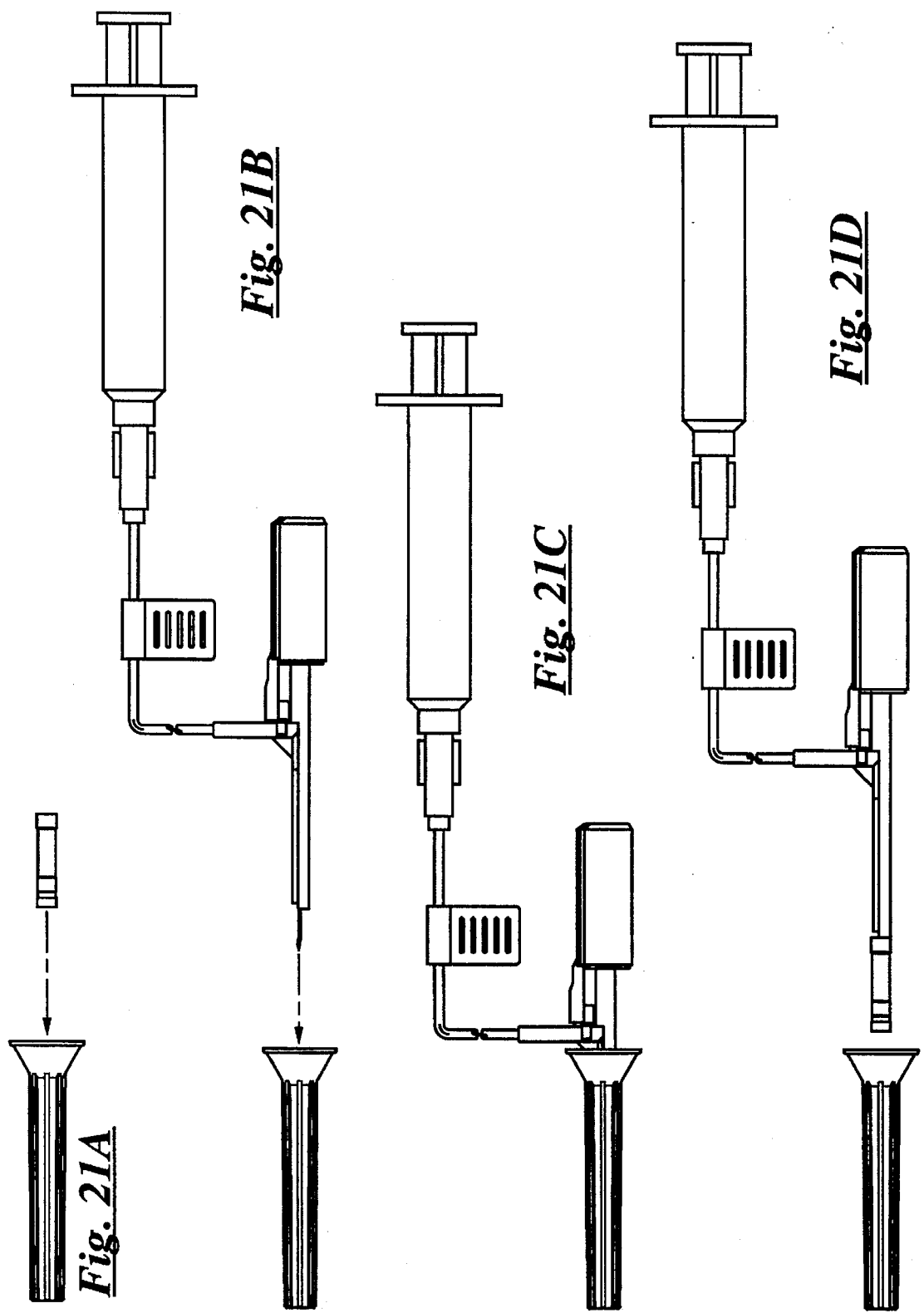

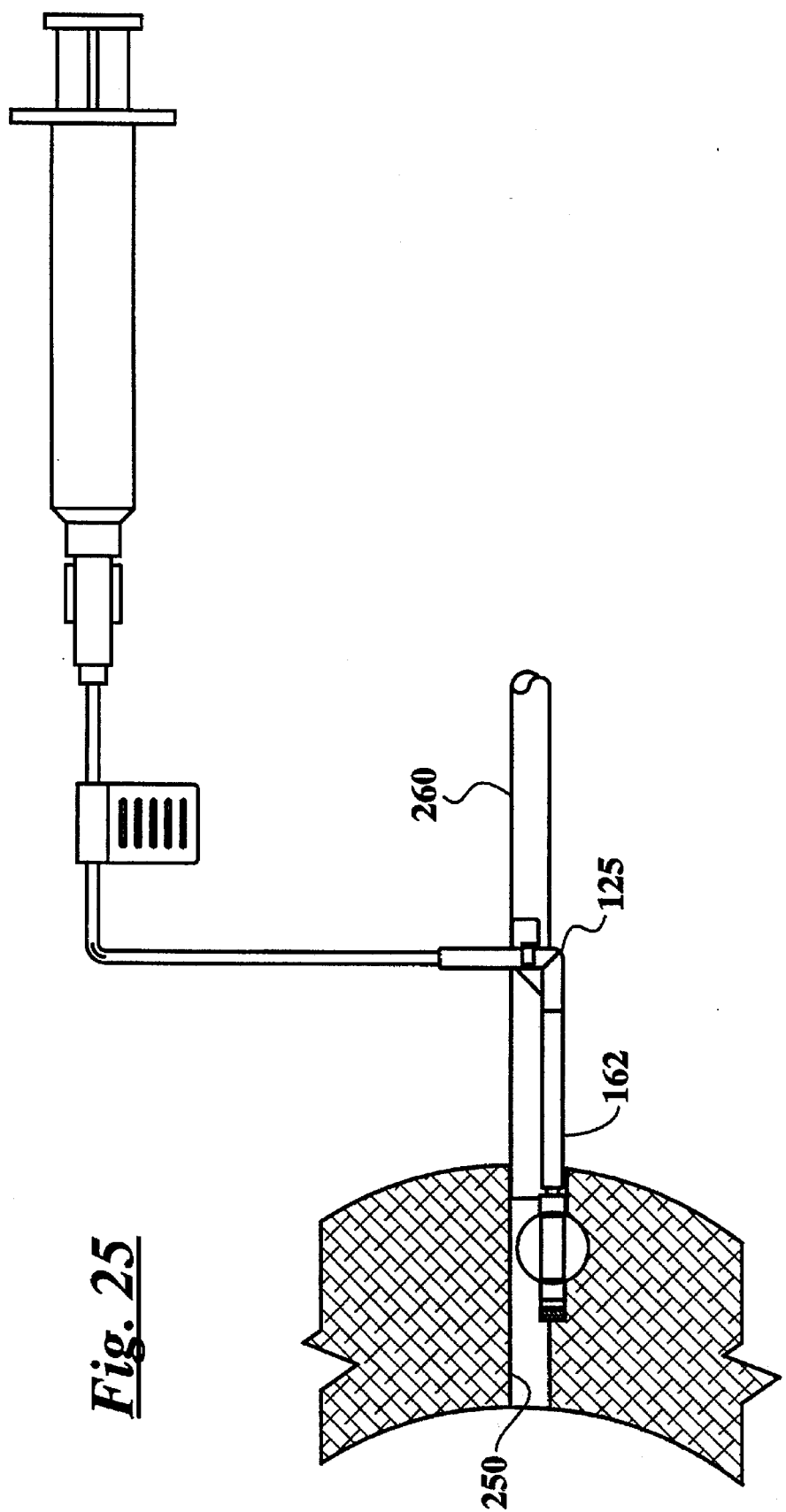

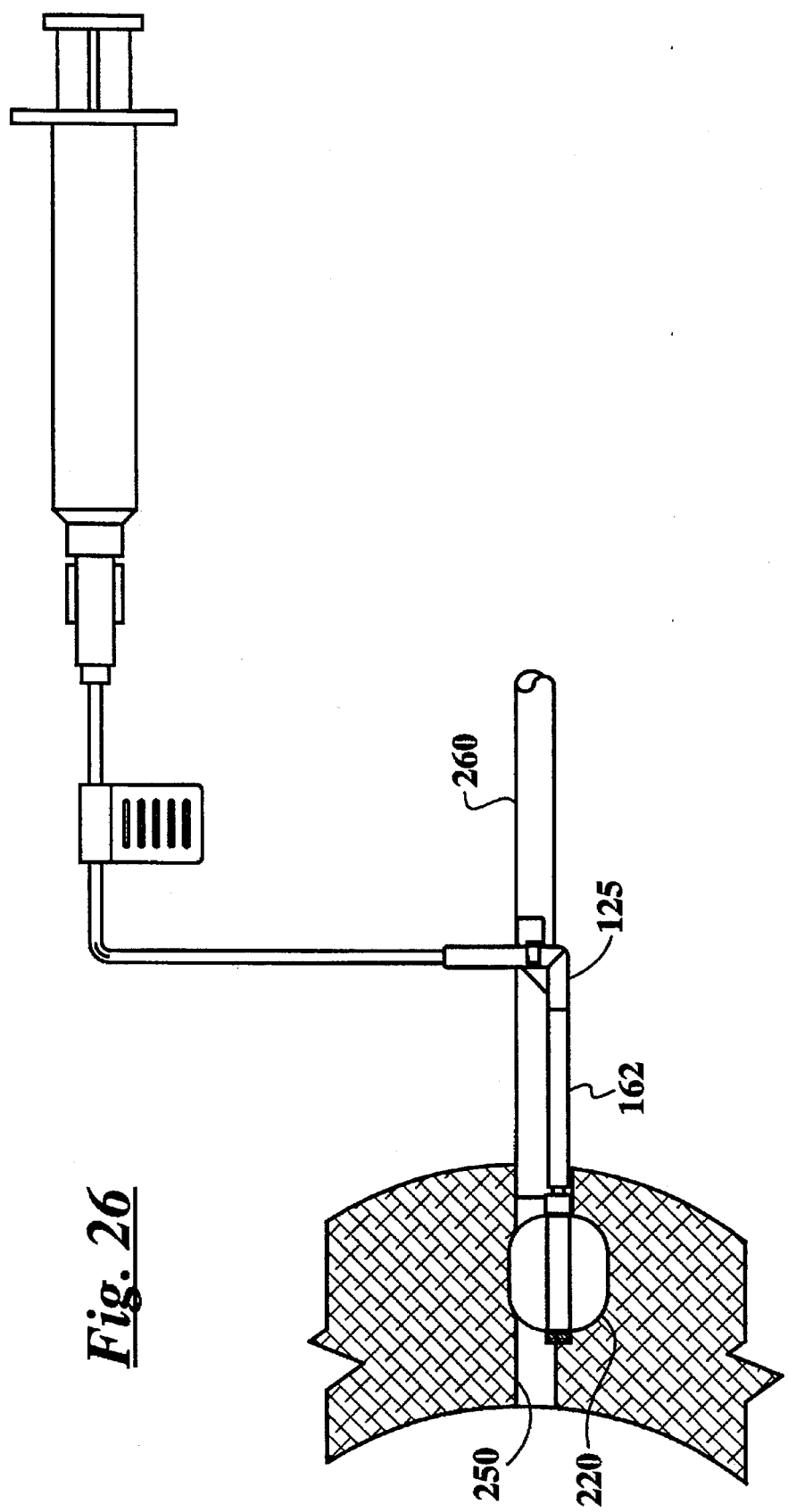

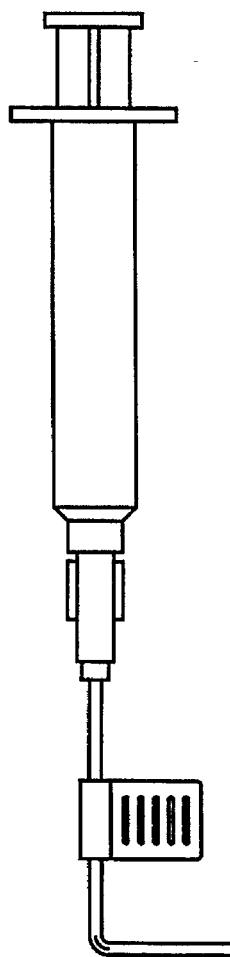
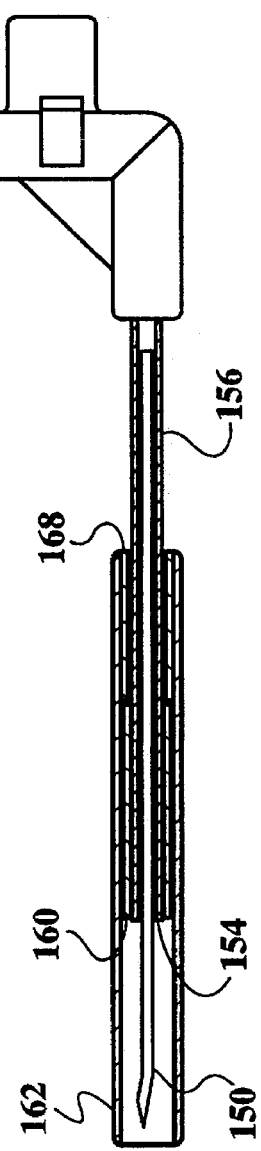
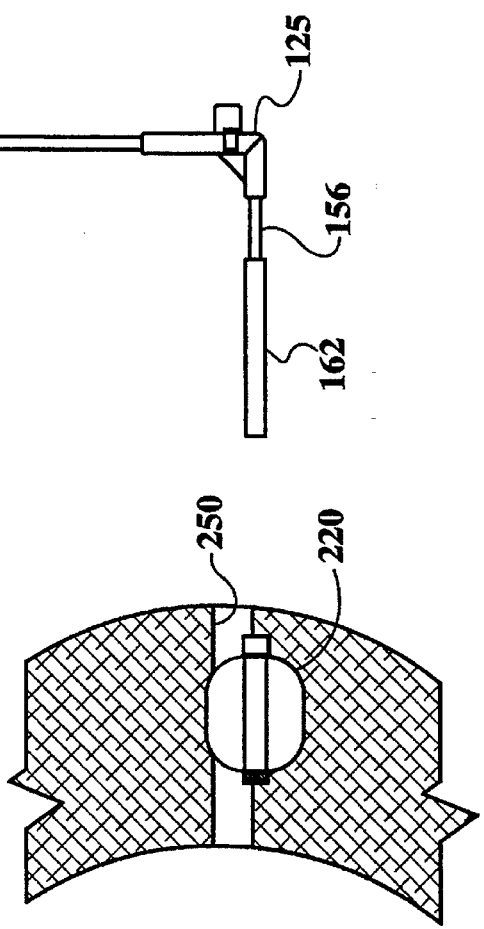
*Fig. 27A*
*Fig. 27B*

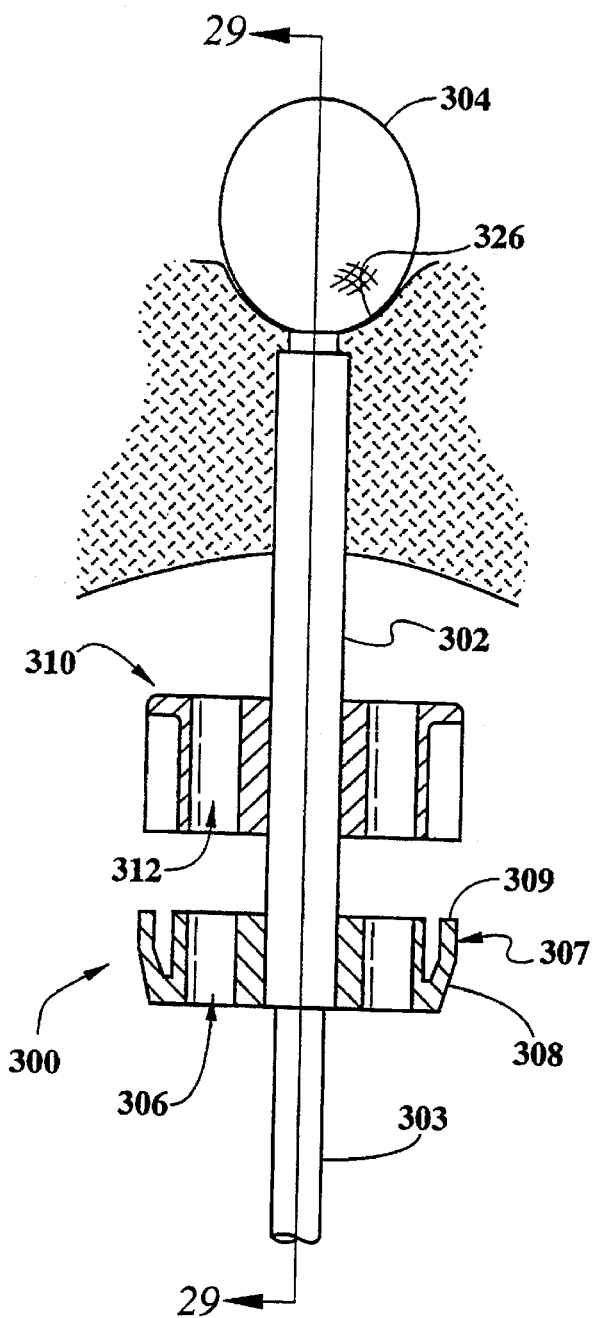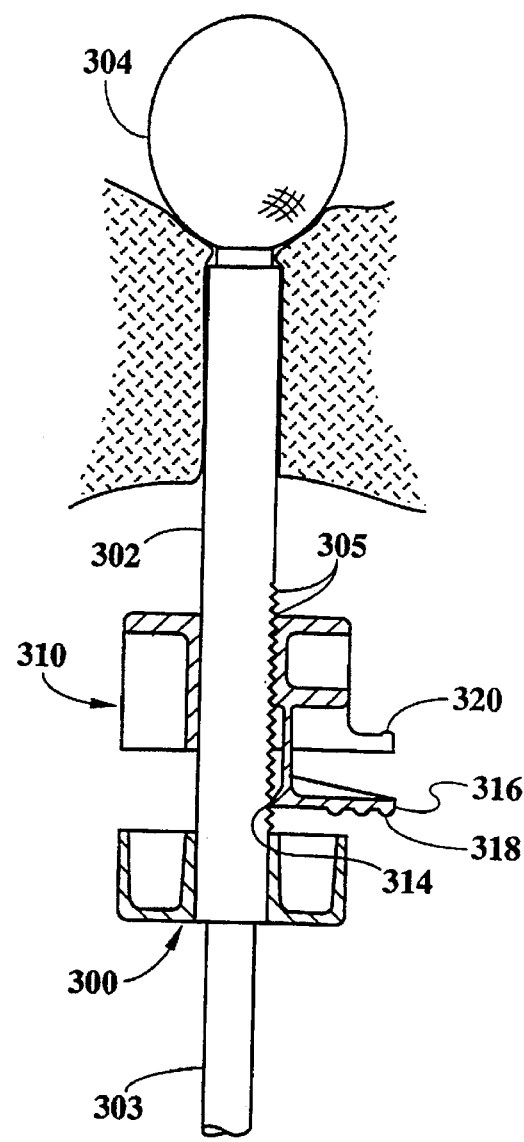
*Fig. 28*  *Fig. 29*

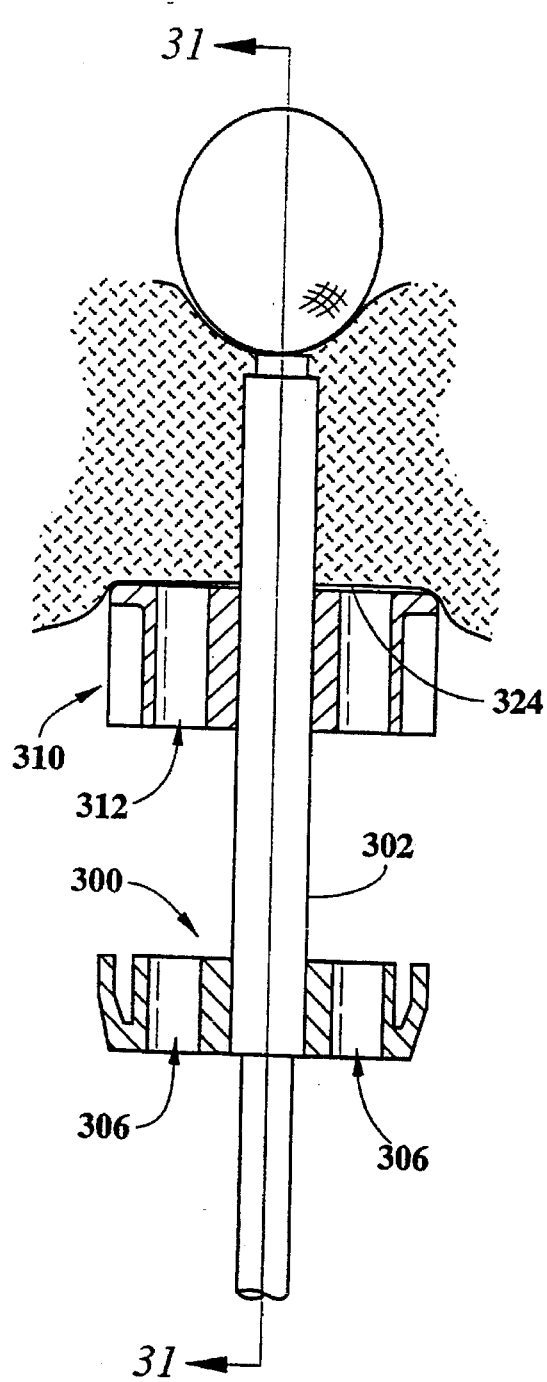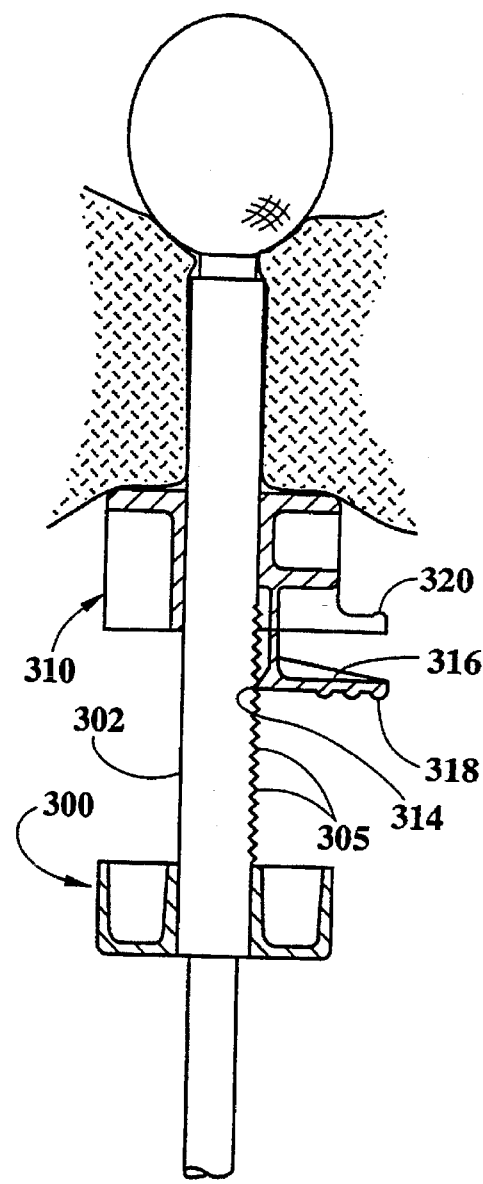
*Fig. 30*  *Fig. 31*

APPARATUS AND METHOD FOR IMPLANTING PROSTHESES WITHIN PERIURETHRAL TISSUES

CROSS-REFERENCE TO RELATED APPLICATION

This application is a continuation-in-part of U.S. patent application Ser. No. 08/120,943, filed Sep. 14, 1993 now U.S. Pat. No. 5,437,603.

TECHNICAL FIELD

The present invention relates generally to medical devices and procedures. More specifically the present invention relates to an apparatus for directing a hypodermic instrument to a predetermined target location within the periurethral tissues and to an apparatus and method for implanting a device or injecting a substance at a predetermined target location within the periurethral tissues.

BACKGROUND OF THE INVENTION

It is known to treat stress urinary incontinence by implanting an inflatable prosthesis within the periurethral tissues. When the prosthesis is properly positioned within the periurethral tissues and inflated, localized tissue volume is increased, enhancing the passive occlusive pressure of the urethral sphincter and thereby achieving continence. Examples of such inflatable prostheses and of instruments for implanting, dispensing, and inflating these prostheses in the periurethral tissues are shown, for example, in U.S. Pat. No. 4,686,962, U.S. Pat. No. 4,773,393, U.S. Pat. No. 4,802,479, and U.S. Pat. No. 4,832,680, which patents are incorporated herein by reference.

Prior art procedures for implanting the inflatable prosthesis in the periurethral tissues comprise forming a first trocar tract to the periurethral tissues on one side of the sphincter. A prosthesis is placed on the tip of a catheter and introduced through this tract to a target location within the periurethral tissues. An isotonic fluid medium is then infused through the catheter and into the prosthesis to inflate it. A second trocar tract is then formed to the periurethral tissues on the other side of the sphincter, and the procedure is repeated with a second prosthesis through the other trocar tract.

Certain difficulties are presented by these prior art implantation procedures. For example, it can be difficult to position the implants properly along the length of the urethra so as to be properly positioned with respect to the sphincter. If the prosthetic devices are not properly positioned with respect to the urethral sphincter, the occlusive pressure will be suboptimal, and continence may not be achieved. Also, the possibility exists that the physician could accidentally puncture the urethra or bladder while implanting the devices. Further, since the trocar tracts are formed independently, the inflation of the first implant can distend the periurethral tissues and push the urethra away from its normal alignment, thereby making the proper positioning of the second implant more difficult.

Finally, the prior art procedure can be somewhat difficult for the physician to perform and may require more than one attempt to properly position the implants, thereby resulting in increased trauma to the patient.

Thus there is a need for an improved apparatus and method for implanting prostheses within periurethral tissues.

There is also a need for an apparatus and method for implanting prostheses within periurethral tissues which will ensure proper positioning of the implants with respect to the urethral sphincter.

Further there is a need for an apparatus and method for implanting prostheses within periurethral tissues which will prevent the possibility of the physician accidentally puncturing the urethra or bladder.

There exists a still further need for an apparatus and method for implanting a pair of prostheses within periurethral tissues in which the implantation of the first prosthesis does not adversely impact the physician's ability to position the second prosthesis properly.

SUMMARY OF THE INVENTION

As will be seen, the present invention overcomes these and other problems associated with prior art methods and delivery instruments for implanting inflatable implants in the periurethral tissues. Stated generally, the present invention comprises an apparatus and method for implanting prostheses within periurethral tissues which ensures proper positioning of the implants with respect to the urethral sphincter. The apparatus and method positively controls the depth and direction of implantation to reduce or eliminate the possibility of accidental puncture or laceration of the urethra or bladder. Furthermore the apparatus and method permit a pair of prostheses to be implanted within periurethral tissues without implantation of the first prosthesis adversely impacting the physician's ability to position the second prosthesis properly.

Stated somewhat more specifically, in a first aspect the present invention comprises an apparatus for guiding a tool along a path in predetermined relation with respect to the urethra of a patient. The apparatus comprises a catheter insertable into the urethra of a patient for placing the urethra in predetermined alignment. A template is operatively associated with the catheter and includes a guide means for directing a tool along a path in predetermined relation to the predetermined alignment. The guide means is operative to direct the tool along the path in predetermined relation with respect to the urethra of the patient.

In a second aspect, the present invention comprises an apparatus for guiding a tool to a predetermined depth with respect to the bladder neck of a patient. The apparatus comprises a catheter having an elongated shaft and being insertable into the urethra of a patient. The catheter comprises an engagement means disposed thereon operative upon the engagement means being introduced into the bladder of the patient for engaging the bladder neck of the patient. A template is operatively associated with the shaft of the catheter at a location in predetermined spaced apart relation to the engagement means of the catheter, whereby when the engagement means engages the bladder neck of the patient the template is located in predetermined location with respect to the bladder neck. The template includes a guide means for directing a tool along a predetermined path, and also includes stop means operatively associated with the guide means for limiting the extent of tool travel along the predetermined path. In this manner, when a tool is directed along the predetermined path and advanced until limited by the stop means, the tool is guided to a predetermined depth with respect to the bladder neck of the patient.

In yet a third aspect, the present invention comprises an apparatus for placing inflatable prostheses within the periurethral tissues of a patient. A template includes first, second, and third guide sleeves having first, second, and third axes respectively, the first and second axes being disposed in predetermined relation to the third axis. The template further includes stop means operatively associated with the first and second guide sleeves. A catheter is inserted through the third guide sleeve of the template and into the urethra of the patient. A balloon adjacent the forward end of the catheter is selectively inflatable when the catheter is inserted into the urethra of the patient to engage the bladder neck of the patient. A catheter stop means operatively associated with the catheter engages the template to locate the template at a location along the catheter in predetermined spaced relation to the balloon. In this manner the template is placed both in predetermined axial alignment with the urethra of the patient and in predetermined spaced relation from the bladder neck of the patient.

A working channel means is inserted through each of the first and second guide sleeves of the template for forming a pair of working channels within the periurethral tissues of the template. Each working channel means includes a stop means which limits the extent of travel of the working channel means with respect to the template such that the working channels are formed to a predetermined depth with respect to the template. A cannula means is then inserted through each of the first and second guide sleeves of the template for introducing an inflatable prosthesis through each working channel. The cannula means is also selectively operable to inflate the inflatable prostheses with a suitable medium. The cannula means includes engagement means for engaging the template so as to limit the depth to which the inflatable prostheses are introduced through the respective working channels. The engagement means also selectively releasably couples the first cannula means to the template.

In still a fourth aspect, the present invention comprises a method for effecting coaptation of a urethra of a patient. A first working channel is formed through the periurethral tissues of the patient to a first target location in predetermined relation to the urethra. A second working channel is then formed through the periurethral tissues of the patient to a second target location in predetermined relation to the urethra and to the first target location. Next, an inflatable prosthesis is inserted through the first working channel to the first target location; and another inflatable prosthesis through the second working channel to the second target location. After both working channels have been formed, the prostheses are inflated such that coaptation of the urethra results.

Thus it is an object of the present invention to provide an improved apparatus and method for implanting prostheses within periurethral tissues.

It is another object of the present invention to provide an improved apparatus and method for directing a hypodermic instrument to a predetermined target location within the periurethral tissues.

A further object of the present invention is to provide an apparatus and method for implanting prostheses within periurethral tissues which will ensure proper positioning of the implants with respect to the urethral sphincter.

Still another object of the present invention is to provide an apparatus and method for implanting prostheses within periurethral tissues which will prevent the possibility of the physician accidentally puncturing the urethra or bladder.

It is yet another object of the present invention to provide an apparatus and method for implanting a pair of prostheses within periurethral tissues in which the implantation of the first prosthesis does not adversely impact the physician's ability to position the second prosthesis accurately.

Other objects, features, and advantages of the present invention will become apparent upon reading the following specification, when taken in conjunction with the drawings and the appended claims.

BRIEF DESCRIPTION OF THE DRAWINGS

The apparatus of the disclosed embodiment is shown in FIGS. 1–14, where:

FIGS. 1A–1E illustrate a template comprising a component of a preferred embodiment of the present invention, where FIG. 1A is a back view of the template, FIG. 1B is a side cut-away view of the template along line 1B—1B of FIG. 1A, FIG. 1C is a front view of the template, FIG. 1D is a side cut-away view of the template along line 1D—1D of FIG. 1C, and FIG. 1E is a top view of the template.

FIG. 3A is an exploded side view of a catheter assembly comprising a component of the preferred embodiment of the apparatus of the present invention, with some subcomponents of the catheter assembly cut away to reveal interior detail; FIG. 3B is a side view of the catheter assembly of FIG. 3A assembled with some subcomponents cut away to reveal interior detail.

FIG. 4A is a side cut-away view of a trocar punch comprising a component of the apparatus of the preferred embodiment; FIG. 4B is an end view of the trocar punch along line 4B—4B of FIG. 4A.

FIG. 5A is a side view of a trocar outer sleeve comprising a component of the apparatus of the preferred embodiment; FIG. 5B is a partial side cutaway view of the trocar outer sleeve of FIG. 5A; and FIG. 5C is an end view of the trocar outer sleeve of FIG. 5A.

FIG. 6A is a side view of a trocar punch assembly of the present invention comprising the trocar punch of FIGS. 4A–4B and the trocar outer sleeve of FIGS. 5A–5C; FIG. 6B is an end view of the trocar punch assembly of FIG. 6A along line 6B—6B of FIG. 6A; and FIG. 6C is cutaway view of the trocar punch assembly of FIG. 6A taken along section line 6C—6C of FIG. 6A.

FIG. 7A is a side cut-away view of a loading cartridge comprising a component of the apparatus of the preferred embodiment; FIG. 7B is an end view of the loading cartridge of FIG. 7A.

FIG. 8 is an exploded view of a cannula subassembly of the disclosed embodiment with some components thereof cut away to reveal interior detail.

FIG. 9 is a top view of a cannula hub of the cannula subassembly of FIG. 8.

FIG. 10 is an assembled view of the cannula subassembly of FIG. 8 partially cut away to reveal interior detail.

FIG. 11A is a side cutaway view of a cannula introducer according to the disclosed embodiment; FIG. 11B is a top view of the cannula introducer of FIG. 11A.

FIG. 12A is a side view depicting the cannula subassembly of FIG. 8 loaded onto the cannula introducer of FIG. 11A; FIG. 12B is a top view of the assembly of FIG. 12A.

Figure 2A:
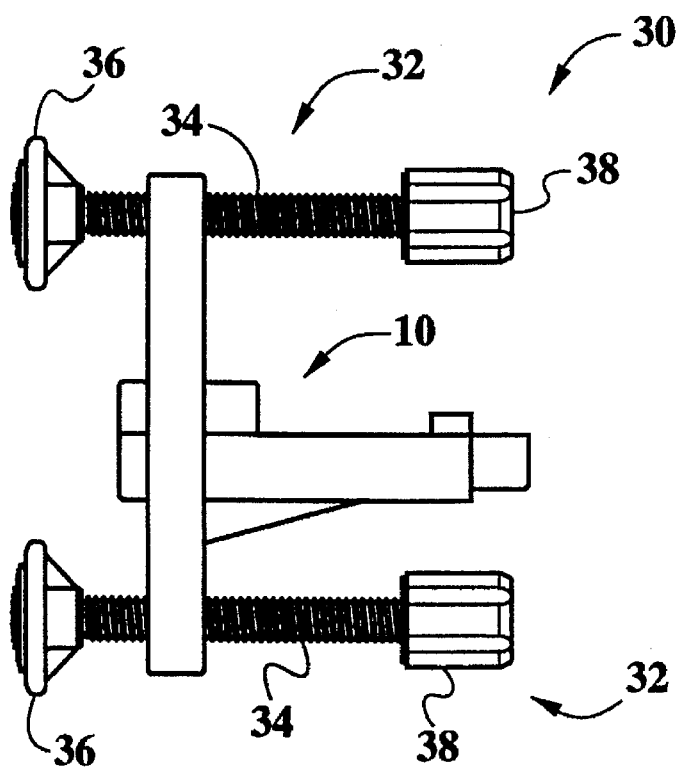
FIG. 2A is a side view of a template assembly comprising the template of FIGS. 1A–E.

The method of the disclosed embodiment is shown in FIGS. 15–27, where:

FIG. 15 shows the assembly of a left-side catheter assembly of FIG. 3A with the template assembly of FIG. 2A, an identical right-side catheter assembly being omitted for clarity.

FIG. 16A is a side view of the assembled catheter assembly and template assembly of FIG. 15; FIG. 16B is a partial cutaway view of the assembly of FIG. 16A.

Figure 17:
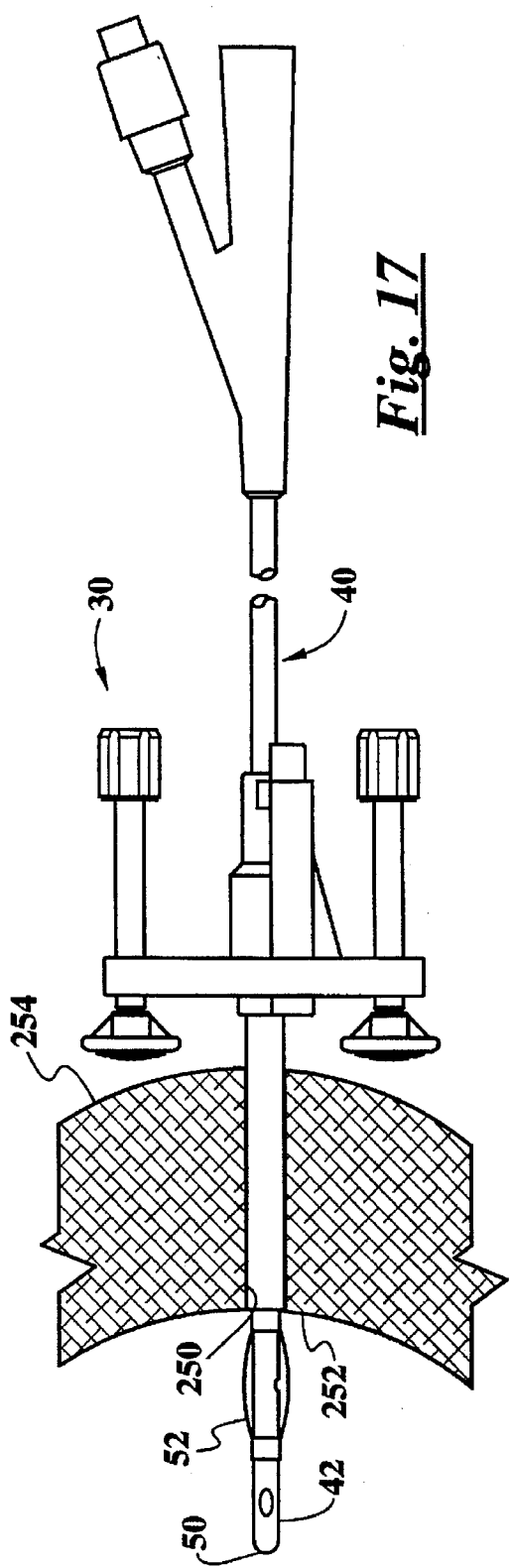

FIG. 17 is a side view of the catheter and template assembly of FIGS. 16A and 16B showing the catheter being inserted into the urethra of a patient.

Figure 18:
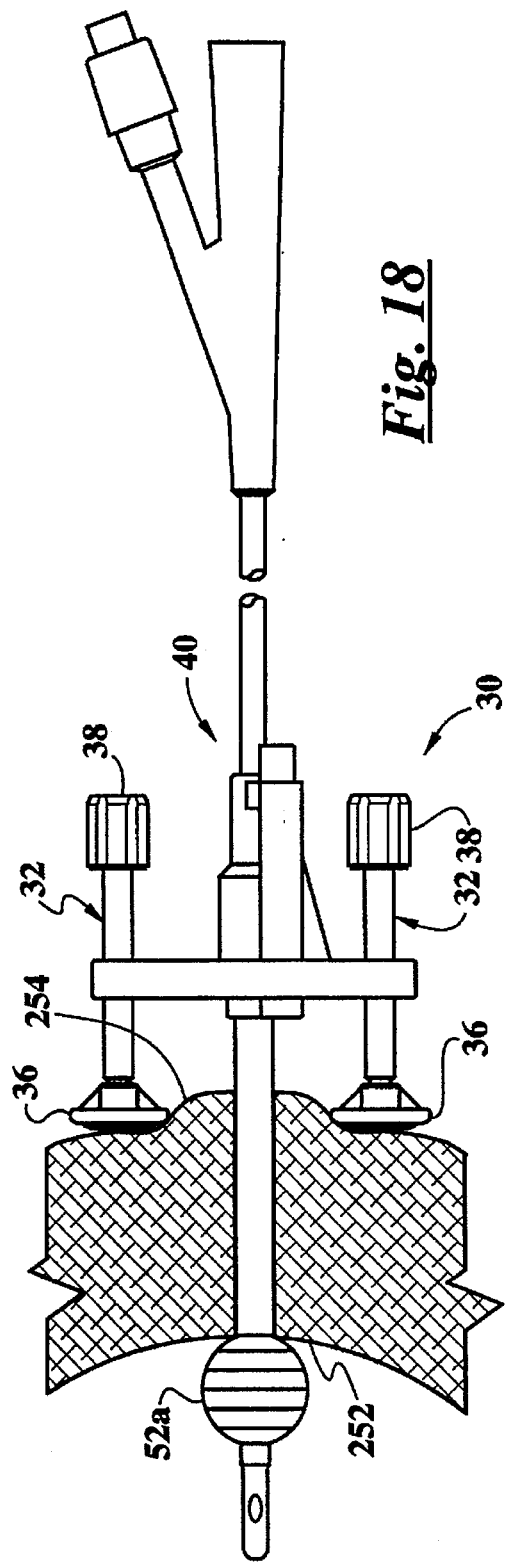

FIG. 18 is a side view of the inserted catheter and template assembly of FIG. 17 showing the balloon of the catheter inflated to engage the bladder neck of the patient.

FIG. 19A is a side view of the inserted and inflated catheter and template assembly of FIG. 18 showing a left-side punch assembly of FIGS. 6A–C being inserted into a channel of the template, an identical right-side punch assembly being omitted for the sake of clarity; FIG. 19B shows the punch assembly inserted through the channel of the template and into the periurethral tissues of the patient; and FIG. 19C is a partial cutaway view of the assembly of FIG. 19B.

FIG. 20 is a side view of the inserted and inflated catheter and template assembly of FIGS. 19A–C showing the punch being withdrawn so as to leave the trocar outer sleeve engaged with the template assembly and having a portion thereof disposed within the periurethral tissues of the patient.

Figure 13:
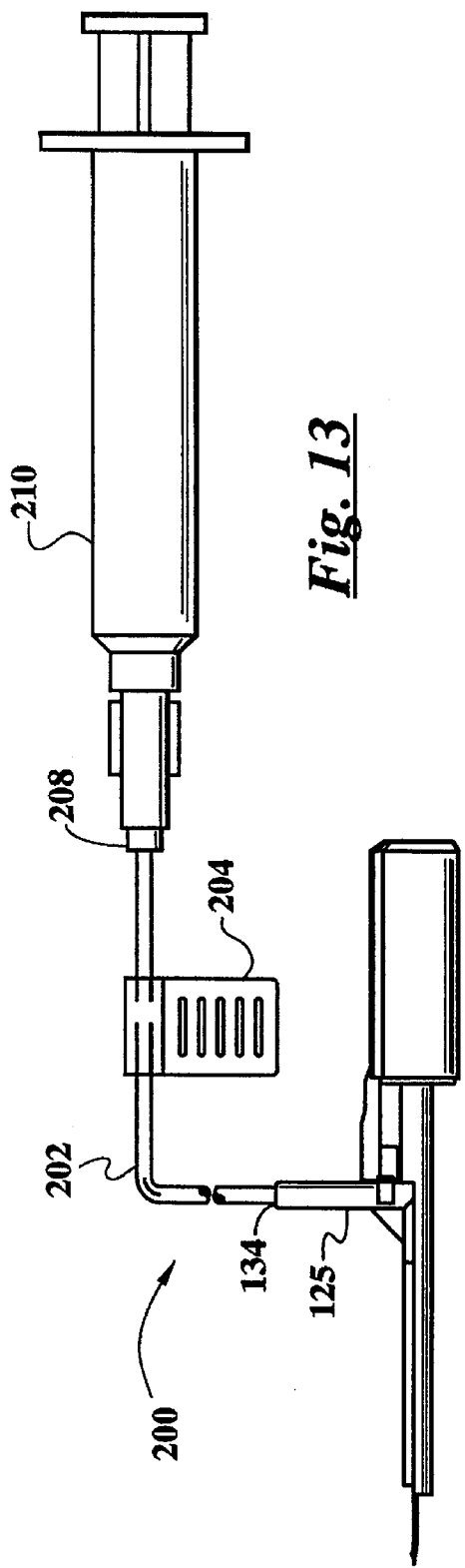
FIG. 13 is a side view of a cannula infusion assembly comprising the cannula subassembly of FIG. 8, loaded onto the cannula introducer of FIG. 11A.
Figure 14B:
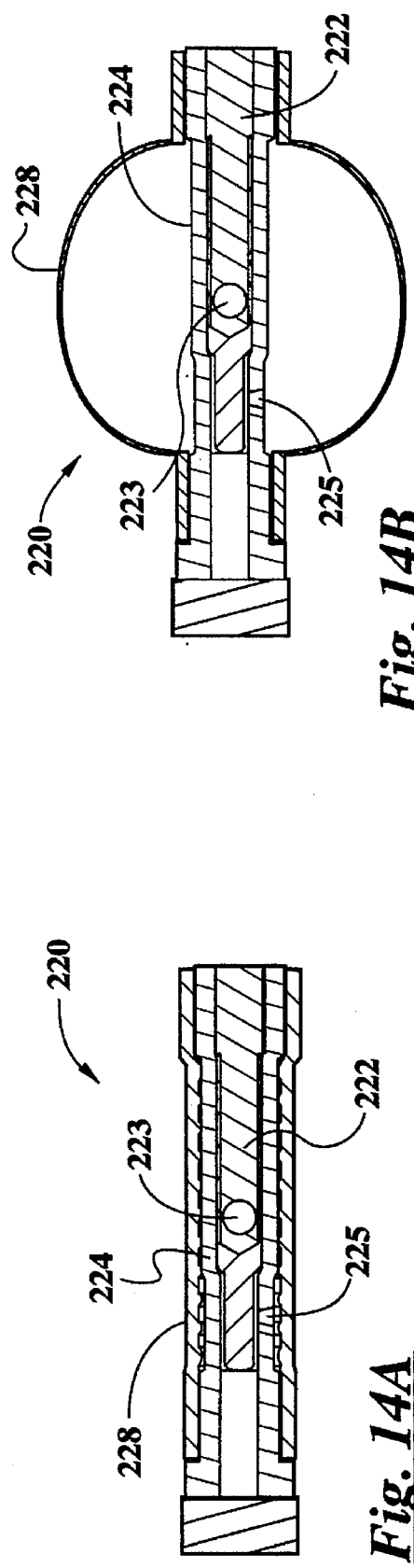
FIG. 14B is a cutaway view showing the inflatable prosthesis of FIG. 14A in an inflated condition.

FIGS. 21A–D are side views depicting the sequence of steps by which the inflatable prosthesis of FIG. 14 is loaded onto a left-side cannula infusion assembly of FIG. 13, an identical right-side cannula infusion assembly and inflatable prosthesis being omitted for reasons of clarity.

Figures 22A, 22B:
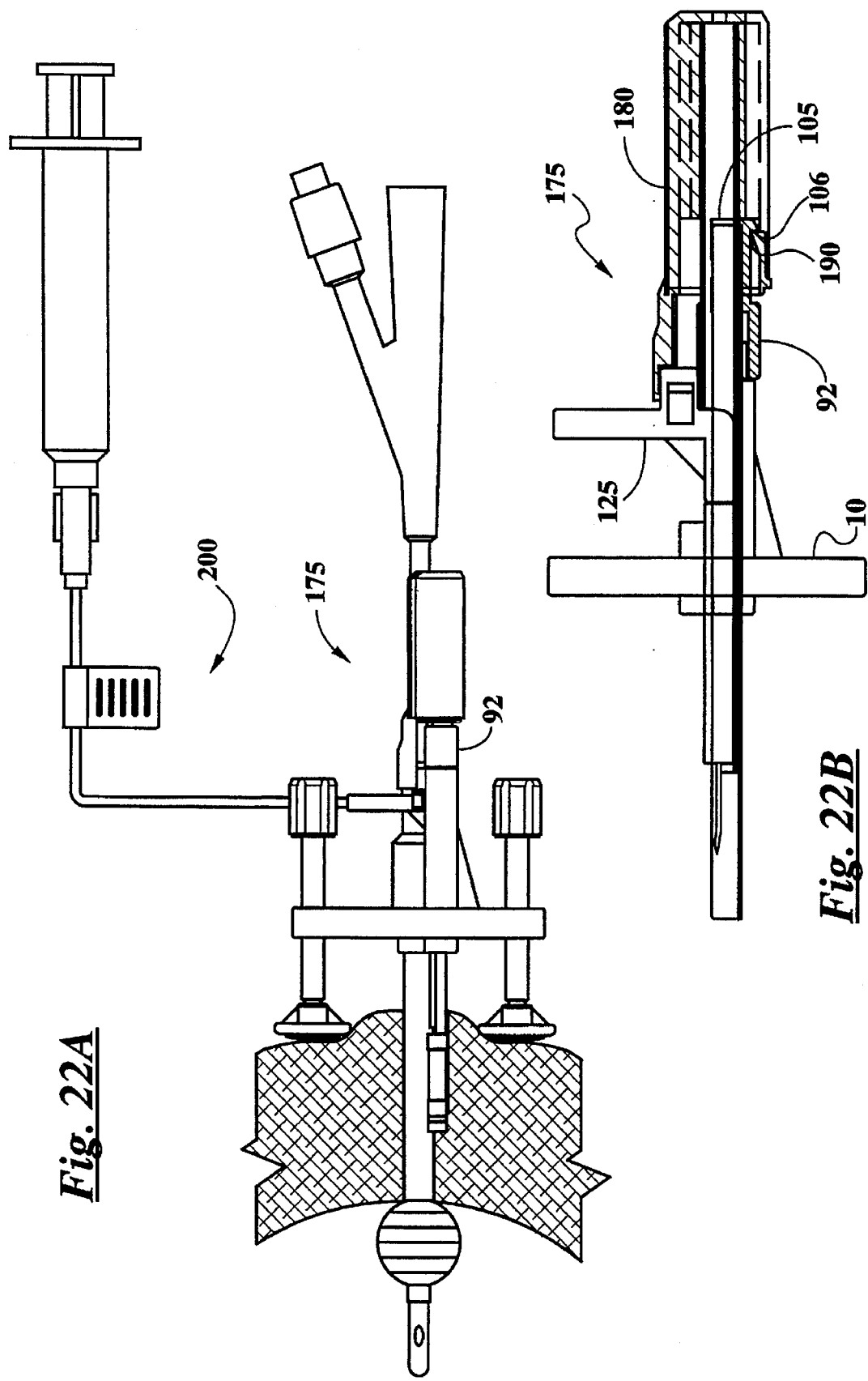

FIG. 22A is a side view of the cannula infusion assembly and associated inflatable prosthesis of FIG. 21D being inserted through the trocar outer sleeve of the assembly of FIG. 20 so as to position the inflatable prosthesis within the periurethral tissues of the patient; FIG. 22B is a side cutaway view of the assembly of FIG. 22A showing detail of the engagement between the cannula infusion assembly and the template assembly; and FIG. 22C is a partial top view of the assembly of FIG. 22A.

Figure 22C:
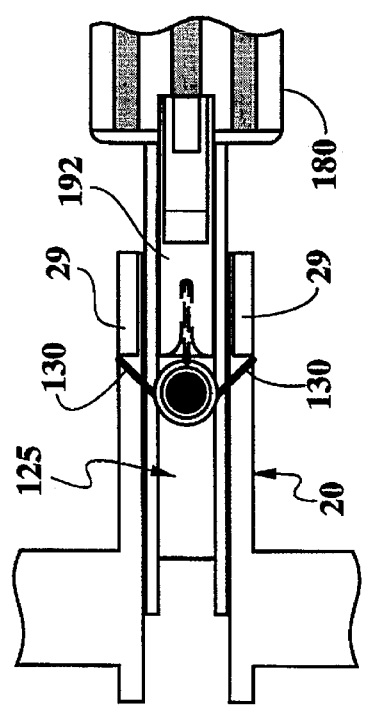
Figure 23:
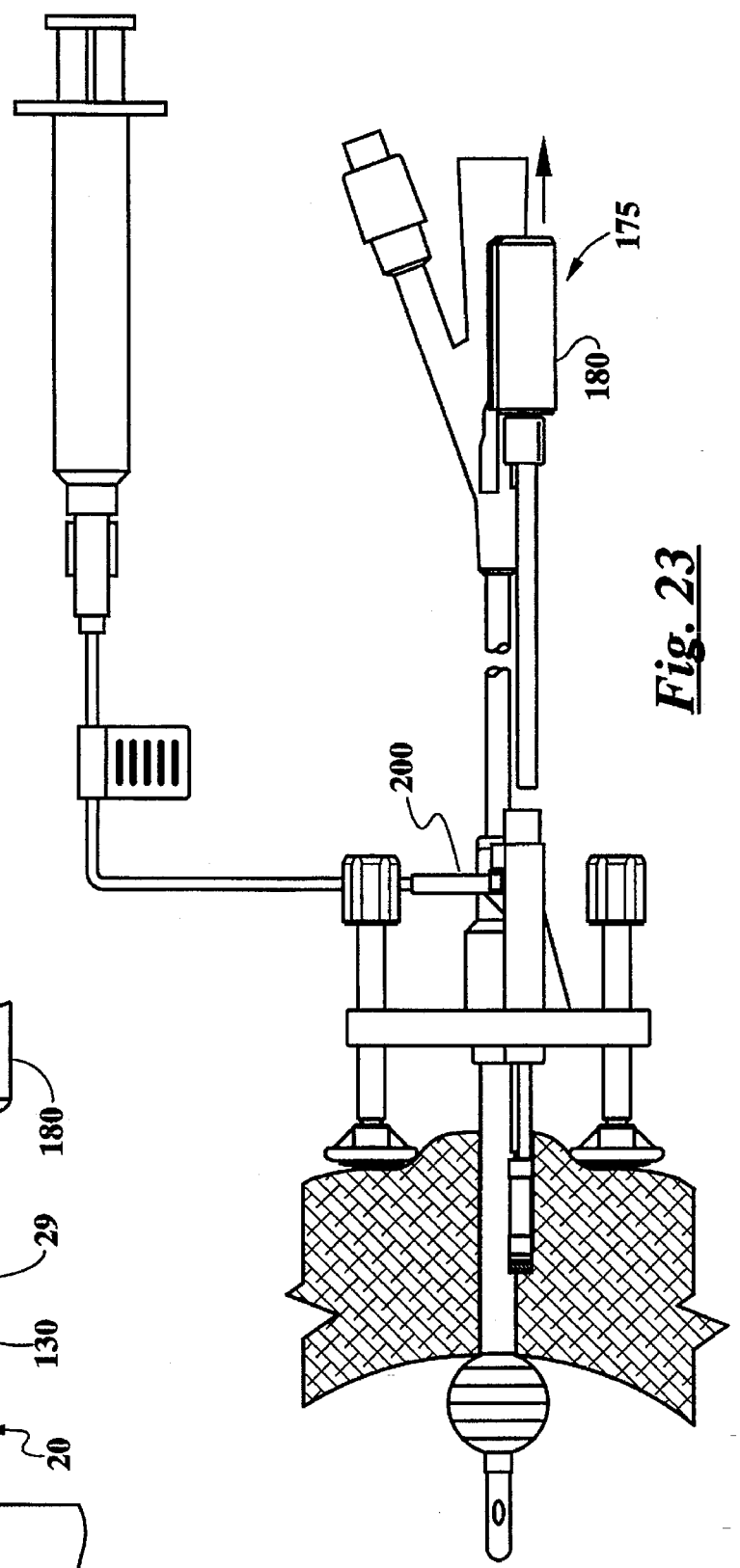

FIG. 23 depicts the withdrawal of the cannula introducer from the assembly of FIGS. 22A–C, leaving the cannula subassembly mounted to the template.

Figure 24:
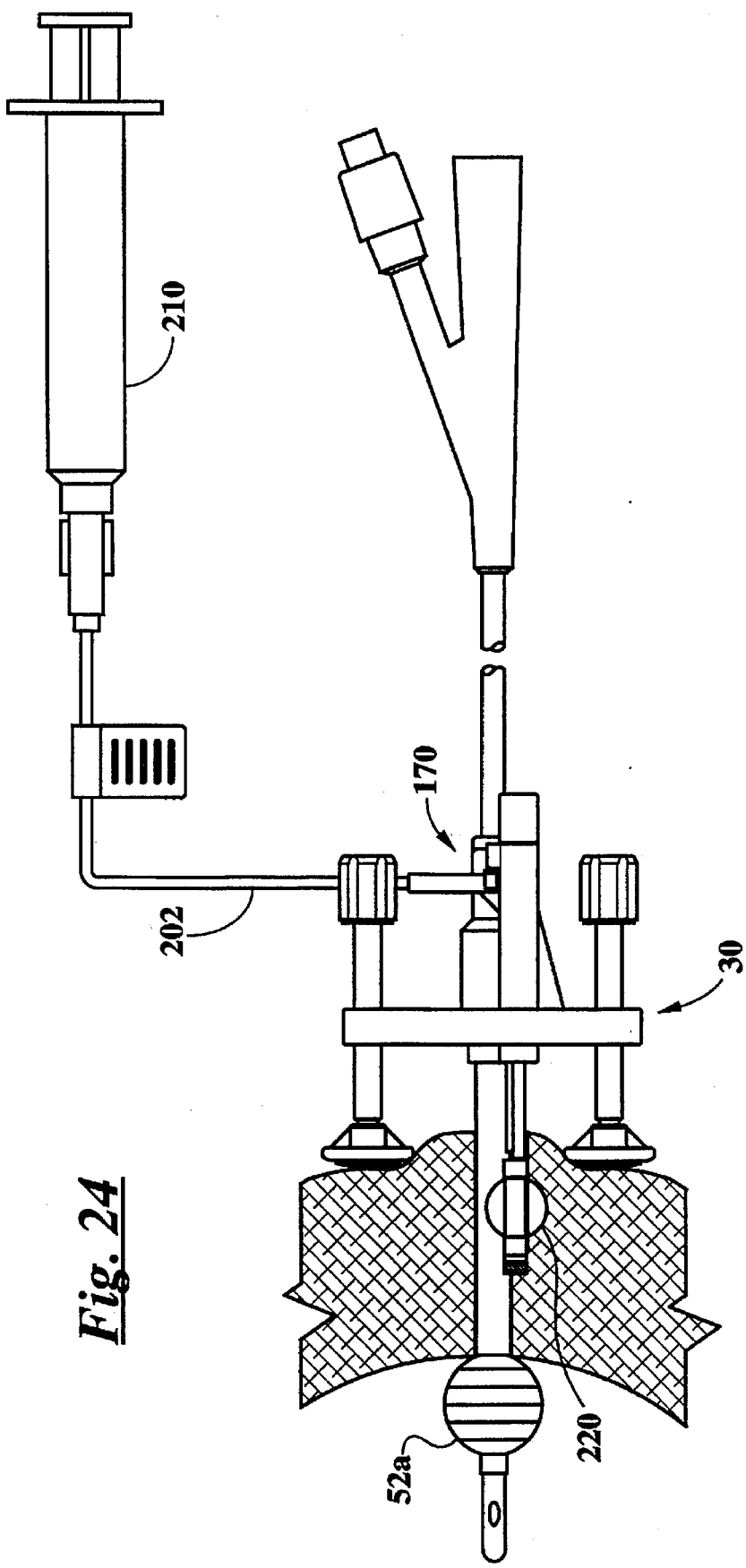

FIG. 24 shows the assembly of FIG. 23 with the prosthesis partially inflated within the periurethral tissues of the patient.

FIG. 25 shows the template assembly being disengaged, leaving the cannula subassembly and partially inflated prosthesis in place within the periurethral tissues of the patient, and a cystoscope being inserted into the urethra of the patient.

FIG. 26 shows the prosthesis being further inflated under cystoscopic guidance until the urethra coapts.

FIG. 27A shows the withdrawal of the cannula subassembly from the patient, leaving the inflated prosthesis implanted within the periurethral tissues of the patient; FIG. 27B is a partial cutaway view of the withdrawn cannula subassembly of FIG. 27A.

FIG. 28 is a top cutaway view of a second embodiment of an apparatus for implanting prostheses within periurethral tissues according to the present invention, with the apparatus in an initial configuration and its balloon catheter inflated within the bladder neck of a patient.

FIG. 29 is a side cutaway view taken along section line 29—29 of FIG. 28.

FIG. 30 is a top cutaway view of the apparatus of FIG. 28 with the apparatus configured to exert a tension on the balloon catheter.

FIG. 31 is a side cutaway view taken along section line 31—31 of FIG. 30.

Figure 32:
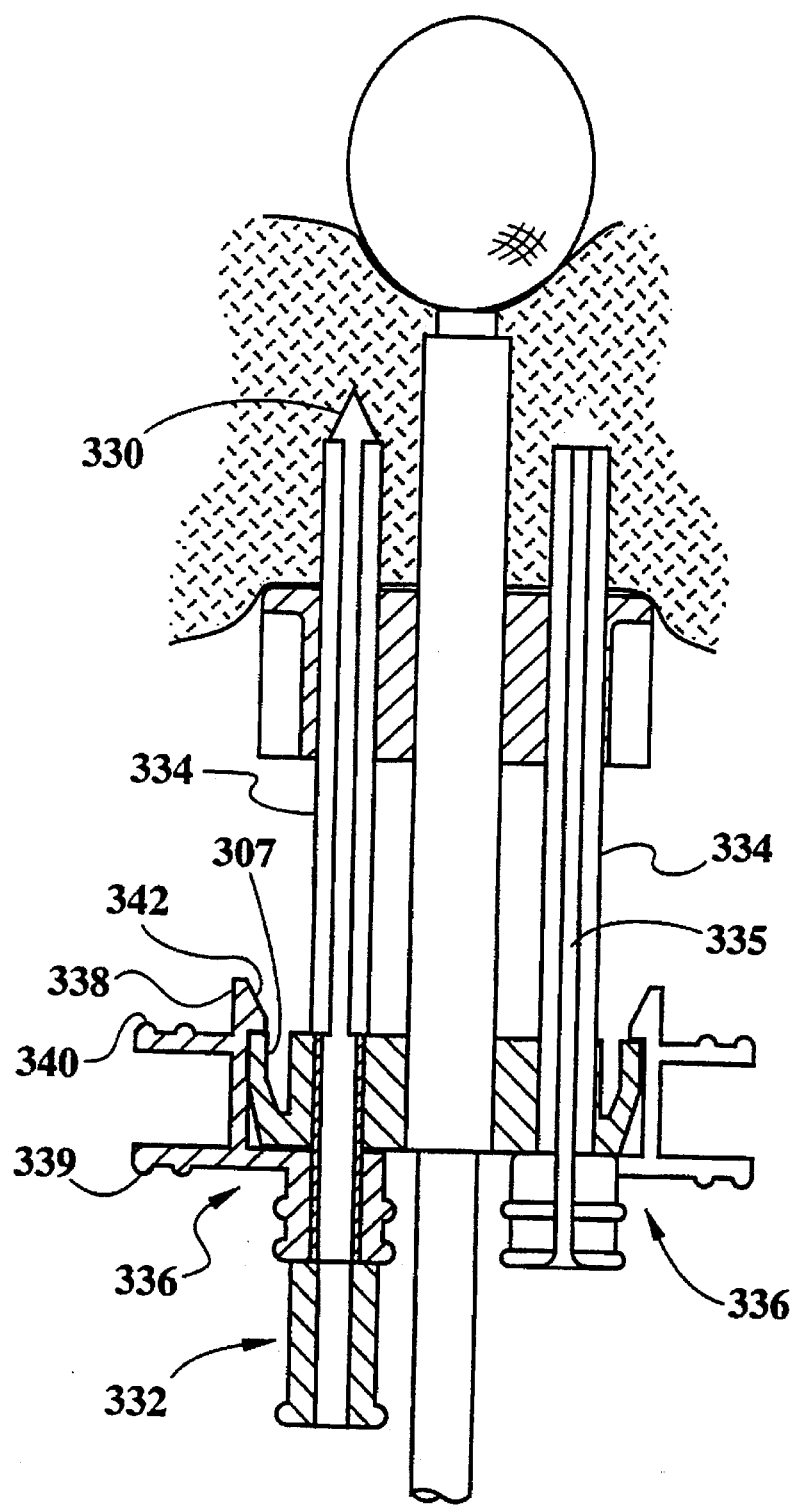

FIG. 32 is a top cutaway view of the apparatus of FIG. 28 illustrating the introduction of a trocar punch into the periurethral tissues of a patient and the subsequent withdrawal of the punch to create a working channel.

Figures 33, 34:
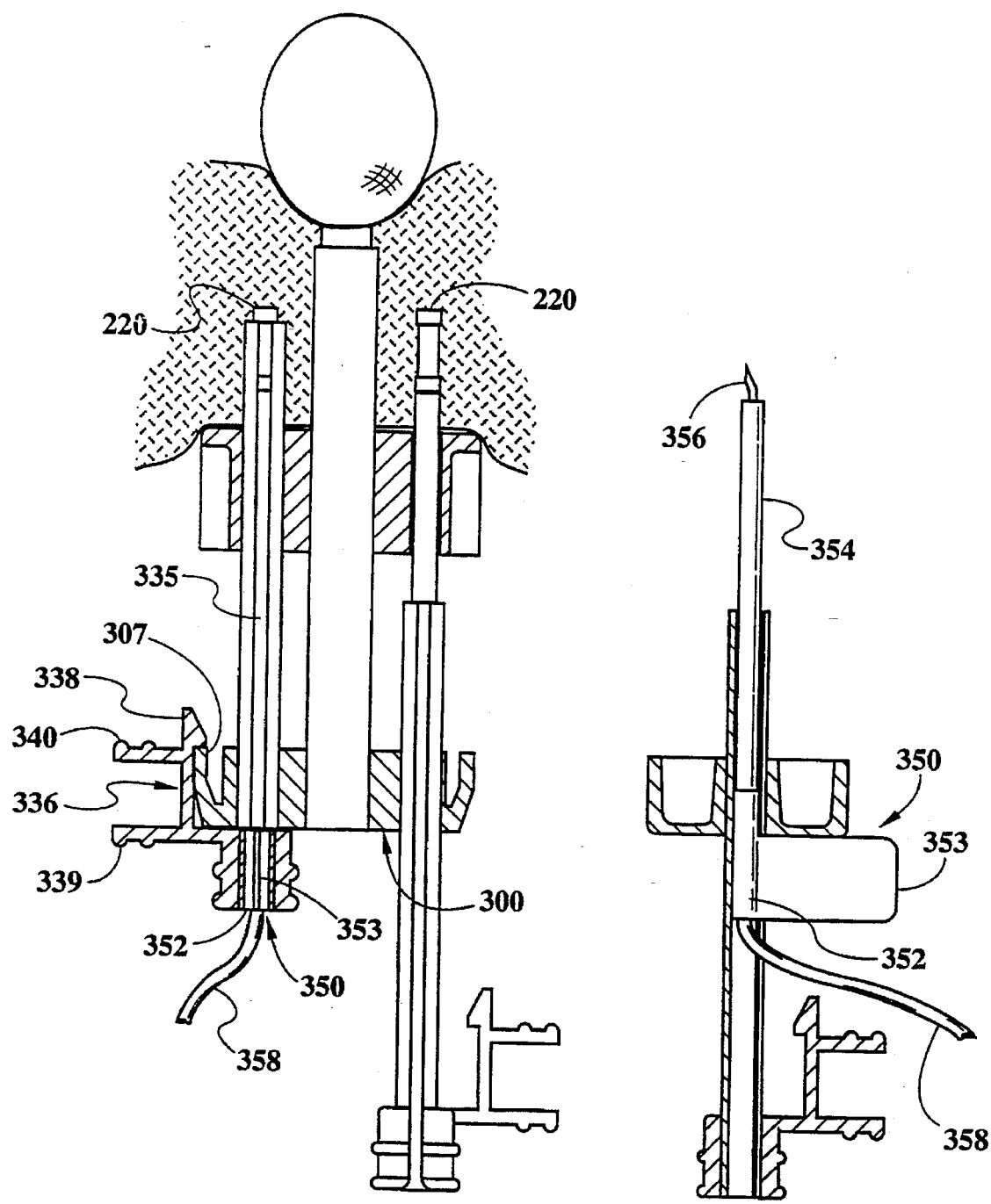

FIG. 33 is a top cutaway view of the apparatus of FIG. 28 showing an inflatable implant advanced through the working channel into the periurethral tissues of a patient, and the subsequent withdrawal of a trocar sleeve to expose the inflatable prostheses within the tissues of the patient prior to inflation.

FIG. 34 is a side cutaway view of an implant carrying subassembly positioned within a trocar sleeve of the apparatus of FIG. 33.

Figures 35, 36:
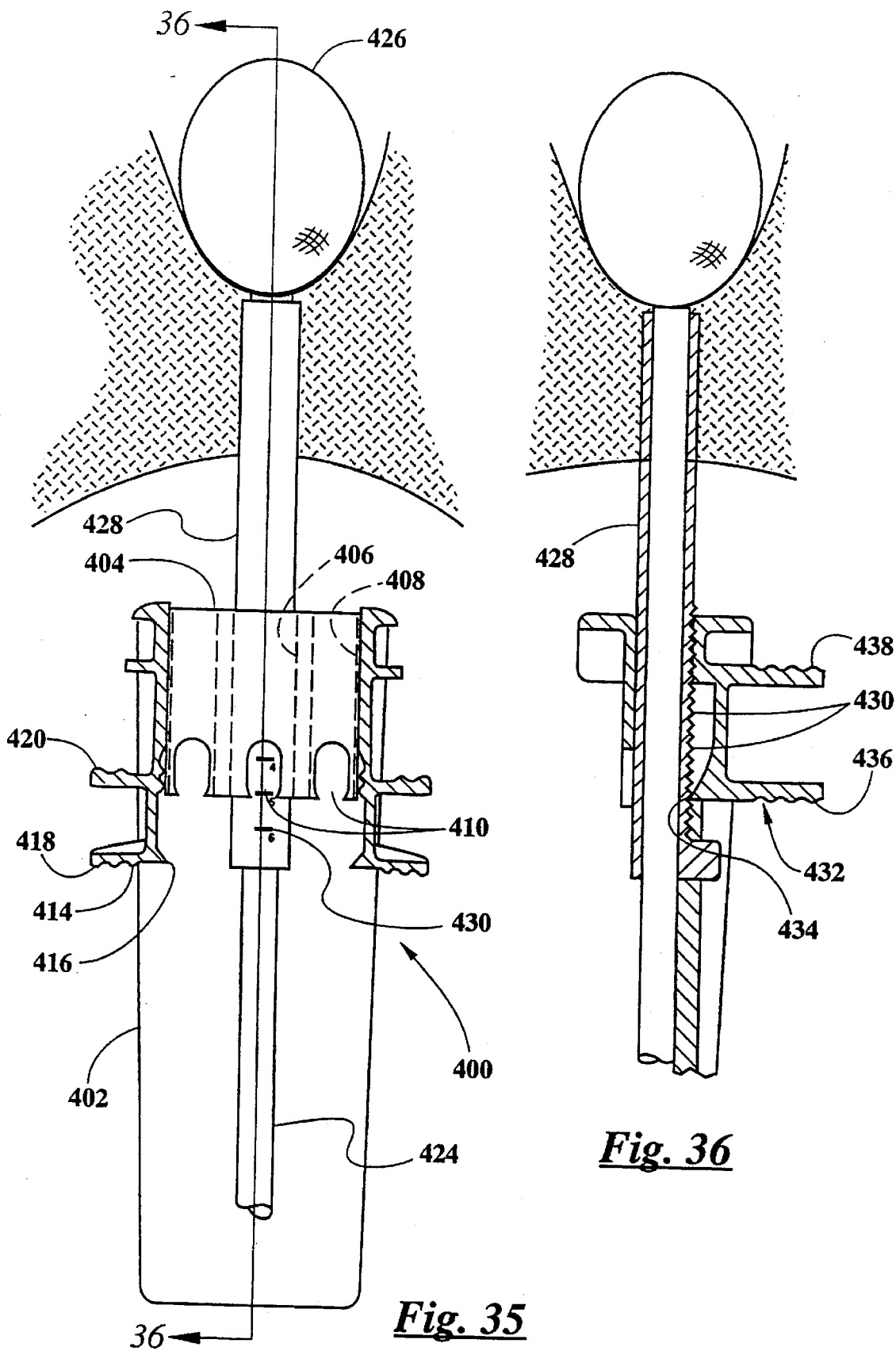

FIG. 35 is a top cutaway view of a third embodiment of an apparatus for implanting prostheses within periurethral tissues according to the present invention, showing a balloon catheter inflated within the bladder neck of a patient.

FIG. 36 is a side cutaway view taken along section line 36—36 of FIG. 35.

Figures 37, 38:
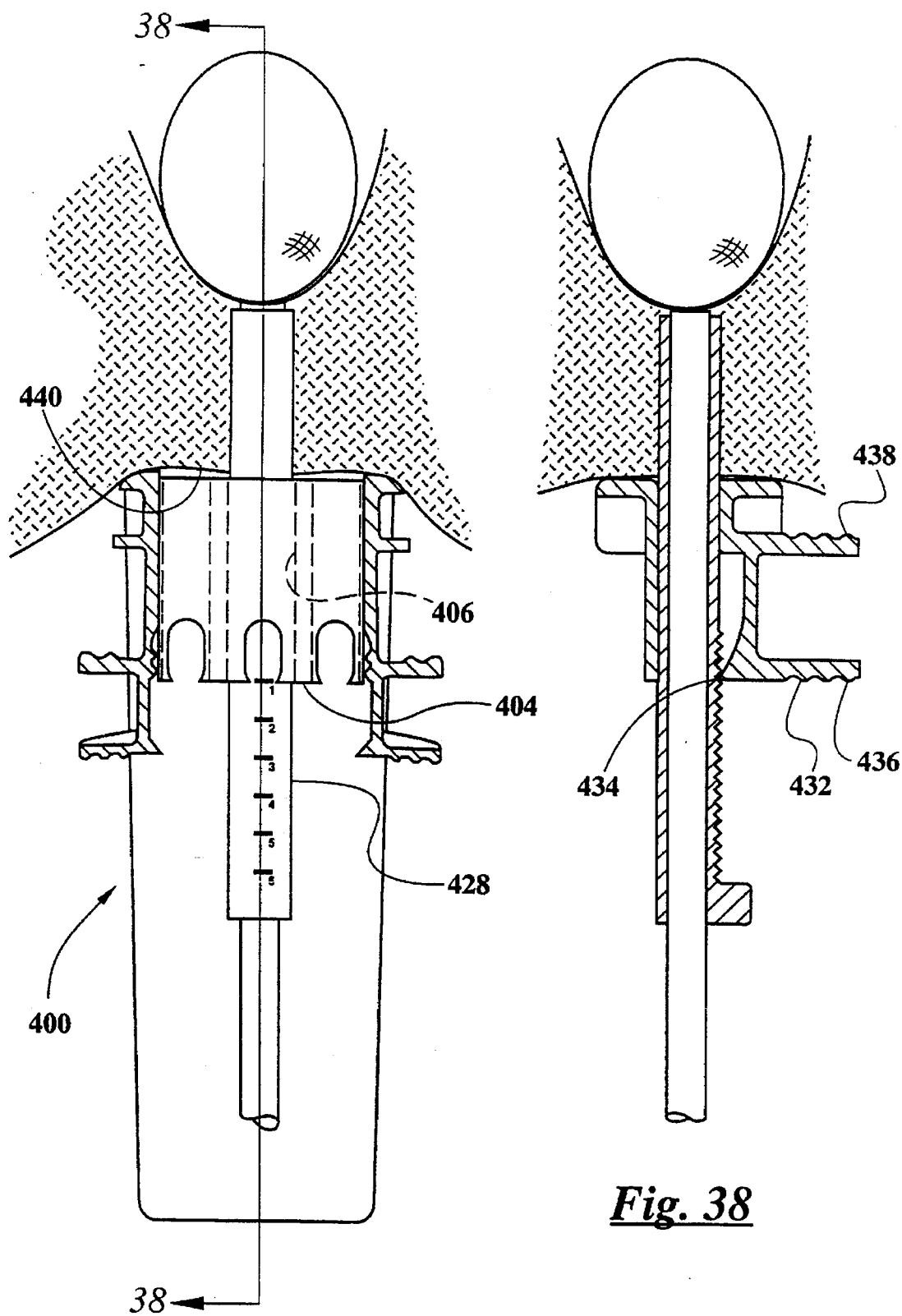

FIG. 37 is a top cutaway view of the apparatus of FIG. 35 showing the template advanced against the introitus of a patient to establish a stable platform exterior of the patient.

FIG. 38 is a side cutaway view taken along section line 38—38 of FIG. 37.

Figures 39, 40:
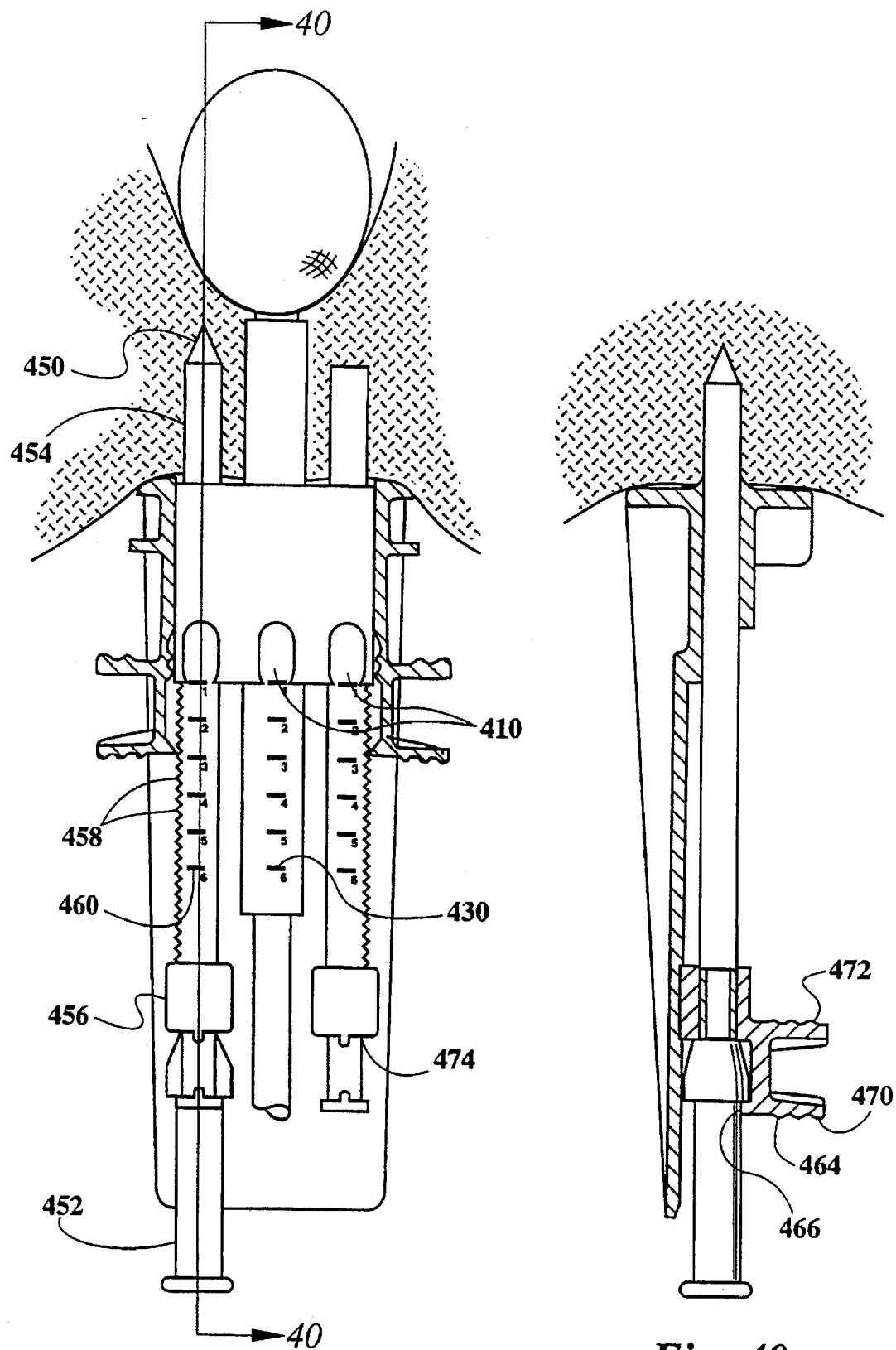

FIG. 39 is a top view of the apparatus of FIG. 35 shown partially cut away and with trocar punches advanced through the template into the periurethral tissues of a patient.

FIG. 40 is a side cutaway view taken along section line 40—40 of FIG. 39.

Figure 41:
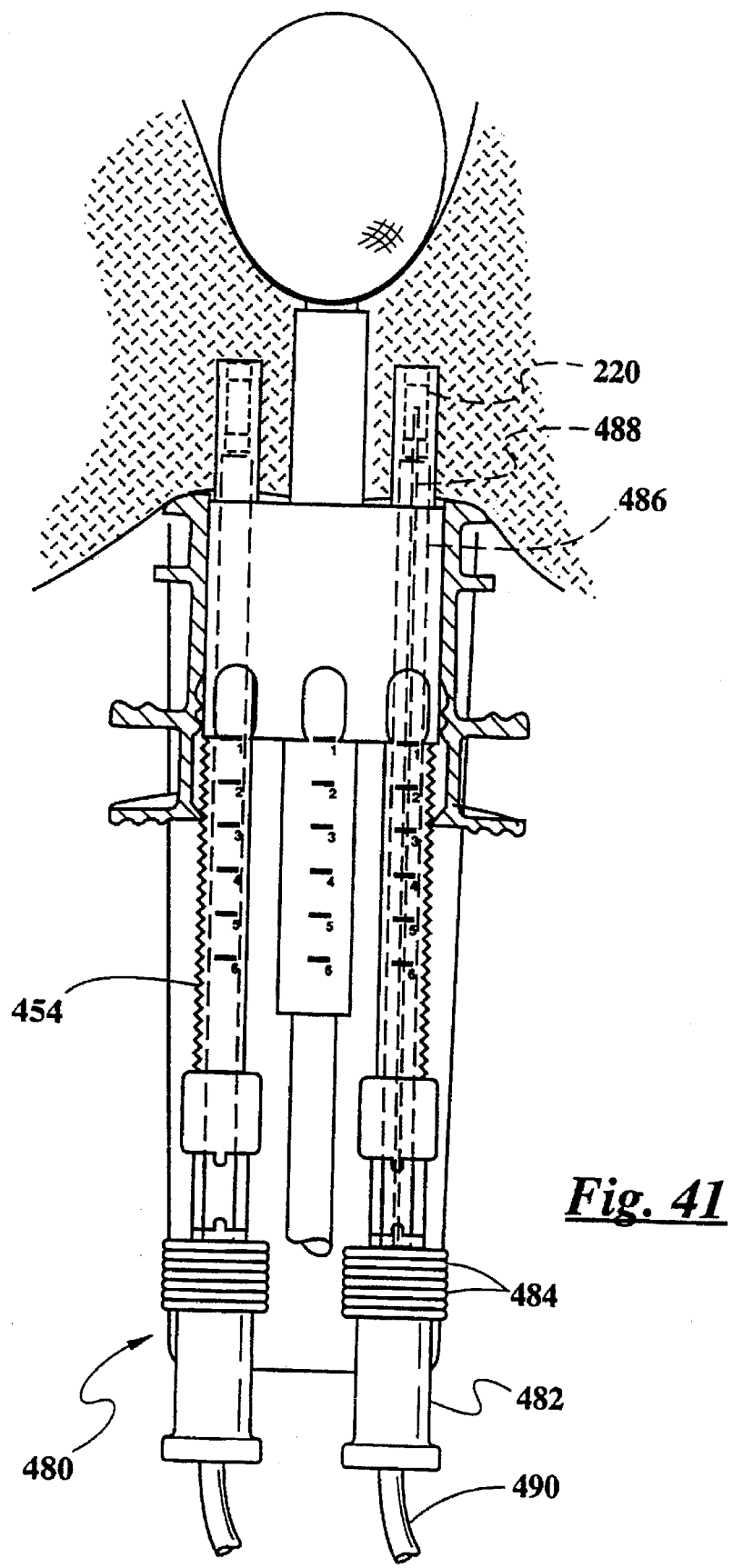

FIG. 41 is a top partial cutaway view of the apparatus of FIG. 35 showing a pair of implant carrying subassemblies positioned within the trocar sleeves.

Figure 42A:
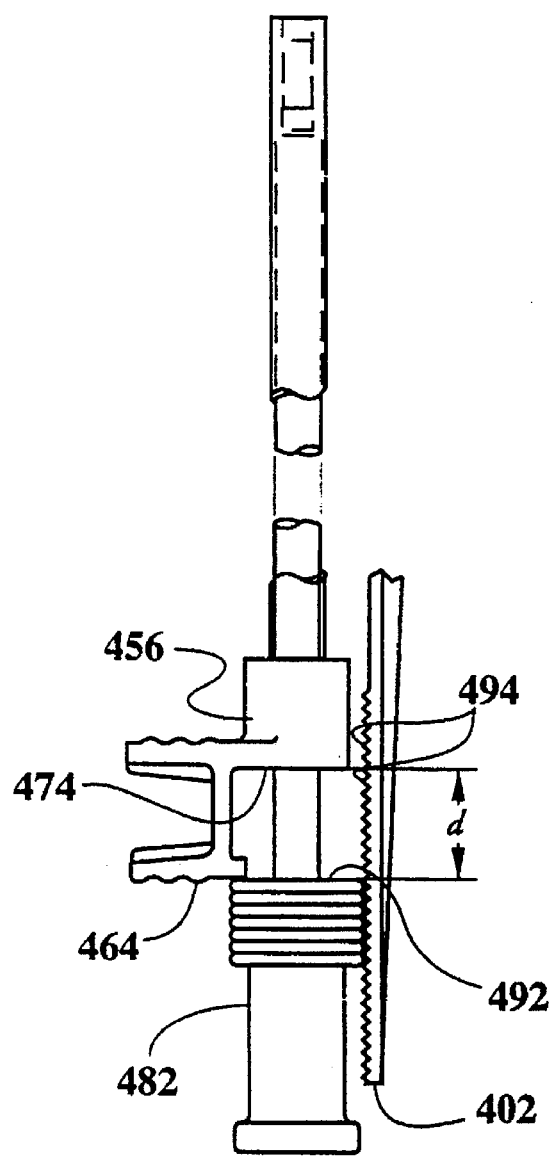
Figure 42B:
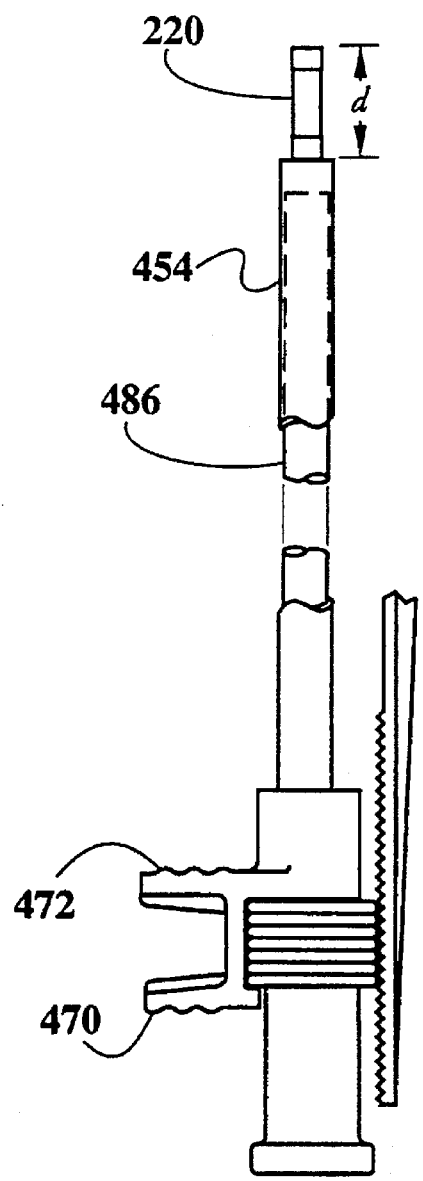

FIG. 42A is a side view of the implant carrying subassembly of the apparatus of FIG. 41 with the hub of the implant carrier subassembly locked in place and the trocar sleeve in its advanced position; FIG. 42B shows the implant carrier subassembly of FIG. 42A with the trocar sleeve in its retracted position.

Figure 43:
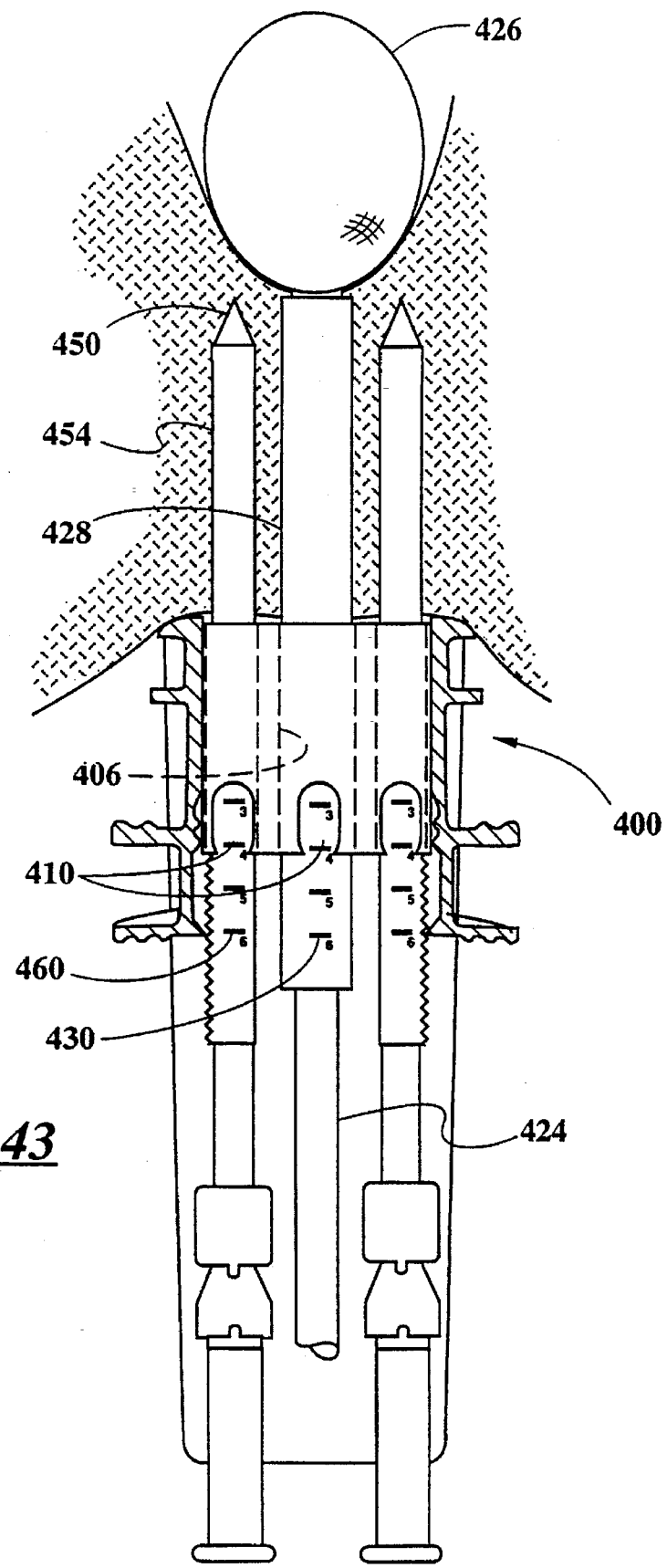

FIG. 43 is a top partial cutaway view of the apparatus of FIG. 35 illustrating use of the apparatus on a patient with a longer urethra.

DETAILED DESCRIPTION OF THE DISCLOSED EMBODIMENT

Referring now in more detail to the drawings, in which like numerals indicate like elements throughout the several views, FIGS. 1A–1E illustrate a template which comprises a component of the guidance device of the disclosed embodiment. The template 10 is comprised of ABS plastic and is an essentially flat member comprising a front face 11 and a back face 12. The template 10 is essentially H-shaped, with two vertically extending arms 13 connected by a horizontal cross-member 14. Threaded bores 15 are formed through each of the arms 13 at their upper and lower ends.

The template 10 comprises a center guide tube 16 disposed at the center of the cross-member 14 and having an axis generally perpendicular to the plane of the back face 12.

The center guide tube 16 comprises a proximal portion 17 extending from the front face 11 of the template and a distal portion 18 extending rearward from the back face 12 of the template. The inner wall 19 of the center guide tube 16 is essentially smooth.

Spaced outward and downward from the center guide tube 16 is an opposed pair of outer guide sleeves 20. Each outer guide sleeve 20 defines an upwardly opening U-shaped channel 22. A main portion 24 of each outer guide sleeve 20 extends rearward from the back face 12 of the template 10. Each outer guide sleeve terminates at a distal end 25. A portion of each center guide sleeve 20 adjacent its distal end 25 comprises a reduced section 26. The wall thickness of the reduced sections 26 is somewhat thinner than the thickness of the remainder of the outer guide sleeves 20 such that the outer dimensions of the reduced sections are somewhat smaller than the outer dimensions of the main guide sleeve portion 24 while the interior dimensions of the reduced sections 26 are equal to the interior dimensions of the main guide sleeve portions 24. A shoulder 28 is formed on each guide sleeve 20 at the junction between the main guide sleeve portion 24 and the reduced portion 26. Upwardly extending tabs 29 are formed at the upper edges of the main body portion 24 of each guide sleeve 20 just forward of the shoulder 28.

Figure 2B:
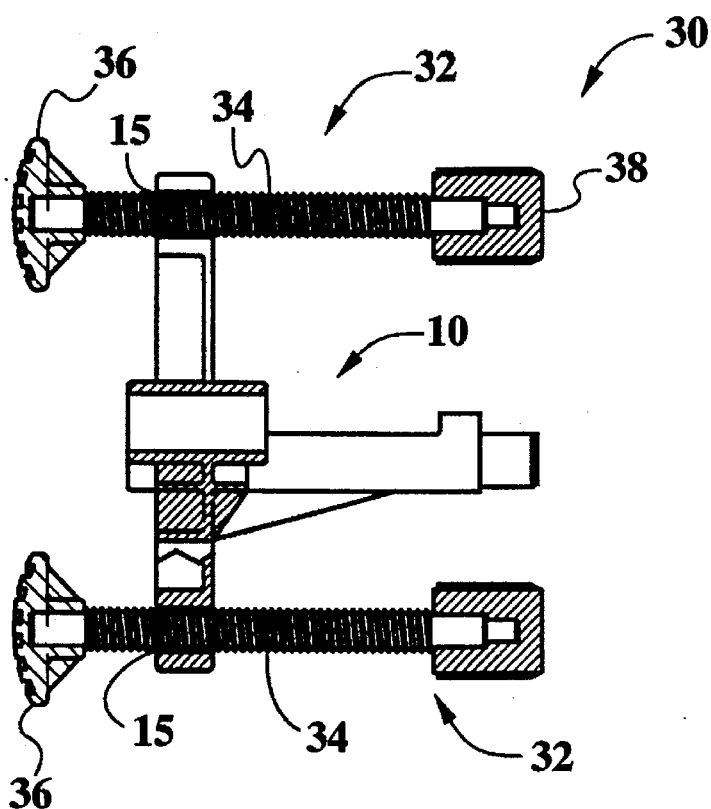
FIG. 2B is a side view of the template assembly of FIG. 2A partially cut away to reveal interior detail.

FIGS. 2A and 2B disclose a template assembly comprising 30 comprising the template 10 with adjustable leg assemblies 32 mounted thereto. Each adjustable leg assembly 32 comprises a threaded rod 34 having a foot pad 36 at its forward end and a thumb screw 38 at its rearward end. The threaded rod 34 of each leg assembly 30 is threaded into a corresponding one of the four threaded bores 15 formed in the corners of the template 10. In the disclosed embodiment the threaded rod 34 is comprised of nylon, the foot pad 36 and thumb screw 38 are molded from ABS plastic, and the foot pad and thumb screw are glued to opposing ends of the threaded rod after the rod has been threaded into the template 10.

FIGS. 3A and 3B show a positioning catheter assembly 40 comprising a positioning catheter 42, an obturator sleeve 44, an obturator sleeve collar 46, and a catheter collar 48. The positioning catheter 42 is a conventional 12 fr. silicone Foley catheter having a shaft 49, a proximal end 50 and a positioning catheter balloon 52 just rearward of the proximal end 50. The obturator sleeve 44 is a tubular member comprised of stainless steel and having an inner diameter approximately equal to the outer diameter of the catheter shaft 49. The obturator sleeve collar 46 is an annular collar comprised of ABS plastic and having an inner diameter equal to the outer diameter of the obturator sleeve 44. In the disclosed embodiment, the obturator sleeve collar 46 is glued onto one end of the obturator sleeve 44. However, it is also possible to form the obturator sleeve collar directly on the obturator sleeve such as by insert molding.

The catheter collar 48 is comprised of silicone and has a longitudinal opening of stepped diameter. At a first section 60 adjacent the forward end 62 of the catheter collar 48 the inner diameter of the catheter collar is somewhat larger than the outer diameter of the obturator sleeve 44, such that when the catheter collar 48 is positioned around the obturator sleeve 44, as shown in FIG. 3B, there is an annular space 63 between the obturator sleeve 44 and the forward end 62 of the catheter collar 48. More specifically, the inner diameter of the catheter collar 48 at the first section 60 is approximately equal to the outer diameter of the distal portion 18 of the center guide tube 16 of the template 10, and the annular space 63 between the obturator sleeve 44 and the forward end 62 of the catheter collar 48 is configured to receive the distal portion 18 of the template center guide tube therewithin.

Rearward of the first section 60 of the catheter collar 48 is a radially inwardly projecting flange 64. The inner diameter of the flange 64 is equal to the outer diameter of the obturator sleeve 44. Rearward of the flange 64 is a second section 66 having an inner diameter equal to the outer diameter of the obturator sleeve collar 46. Rearward of the second section 66 is a third second 68 having an inner diameter approximately equal to the outer diameter of the catheter shaft 49. The stepped transition between the second section 66 and the third section 68 defines a shoulder 69.

To assemble the positioning catheter assembly 40, the obturator sleeve collar 46 is glued to the distal end of the obturator sleeve 44. The catheter collar 48 is bonded to the catheter shaft 49 with a silicone adhesive or other suitable fastening arrangement. The proximal end 50 of the positioning catheter 42 is then inserted through the distal end of the obturator sleeve 44 and advanced until the obturator sleeve collar 46 enters the first section 60 of the catheter collar 48. As the positioning catheter 42 is advanced further, the obturator sleeve collar 46 advances past the inwardly extending annular flange 64 of the catheter collar 48 and into the third section 68 of the catheter collar. The shoulder 69 between the second and third sections 66, 68 of the catheter collar 48 serves as a positive stop to limit further advancement of the positioning catheter 42 with respect to the obturator sleeve 44. In this position, the inwardly extending annular flange 64 of the catheter collar 48 captures the obturator sleeve collar 46 and positively locks the positioning catheter 42 with respect to the obturator sleeve 44.

Referring now to FIGS. 4A and 4B, a trocar punch 74 comprises a shaft 76 and a trocar handle 78. The shaft 76 of the trocar punch 74 is comprised of stainless steel and has a sharpened proximal end 80. The trocar handle 78 is molded from ABS plastic and is secured to the distal end of the shaft 76 by insert molding, glue, or other suitable means. An annular recess 82 is formed at the forward end of the trocar handle 78 between an inner handle wall 84 and the shaft 76 of the punch 74. The annular recess 82 terminates in a base wall 86 at the rearward end of the recess. As shown in FIG. 4B, the inner wall 82 at the forward end of the trocar handle 78 has a pair of opposed, inwardly extending projections 88, the function and purpose of which will be explained below.

FIGS. 5A and 5B show a trocar outer sleeve 90. The trocar outer sleeve 90 is comprised of stainless steel and has a trocar outer sleeve adapter 92 secured to its distal end. The trocar outer sleeve adapter 92 is comprised of ABS plastic and is secured to the trocar outer sleeve 90 by insert molding, glue, or other suitable means. The trocar outer sleeve adapter 92 has a front end 93. A forward portion 94 of the trocar outer sleeve adapter 92 adjacent its front end 93 is U-shaped in cross-section, with walls circumscribing an arc of slightly greater than 180°. The inner wall 96 of the forward portion 94 of the trocar outer sleeve adapter 92 is spaced apart from the trocar outer sleeve 90 so as to form a recess 98 therebetween.

The distal portion 102 of the trocar outer sleeve adapter 92 has a smaller outer diameter than the forward portion 94. Like the forward portion 94, the distal portion 102 is essentially U-shaped in cross-section, each of the side walls of the distal portion terminating in an upper edge 104. At the lower edge of the rearward end 105 of the trocar outer sleeve adapter 92, a flange 106 is formed. The bottom surface 108 of the flange 106 is beveled downward and forward.

FIGS. 6A–6C disclose a trocar assembly 110 comprising a trocar punch 74 and a trocar outer sleeve 90. The shaft 76 of the trocar punch 74 is nested within the trocar outer sleeve 90, and the distal portion 102 of the trocar outer sleeve adapter 92 is received within the annular space 84 in the forward end 82 of the trocar handle 78. The rearward end 105 of the trocar outer sleeve adapter 92 abuts the base 84 of the annular recess 82 in the trocar handle 78. As shown in FIG. 6C, the upper edges 104 of the distal portion 102 of the trocar outer sleeve adapter 92 are captured beneath the projections 86 formed on the inner wall of the trocar handle 78 and thereby prevent relative rotation between the trocar punch 74 and the trocar outer sleeve 90. Also, because the U-shaped walls of the trocar outer sleeve 90 circumscribe an arc of greater than 180°, the shaft 76 of the trocar punch 74 is retained within the outer sleeve and thereby prevented from becoming laterally disengaged.

Referring now to FIG. 7, a loading cartridge 114 is illustrated. The loading cartridge 114 comprises a tubular body 116 which is closed at one end 118 and which has a tapered lead-in 120 at the other. The tubular body 116 of the loading cartridge 114 includes interior walls 124. In the disclosed embodiment, the loading cartridge 114 is comprised of styrene plastic. The purpose and function of the loading cartridge 114 will be explained below in conjunction with a discussion of the operation of the invention.

Referring now to FIGS. 8 and 9, a cannula hub 125 comprises an L-shaped body portion 126 comprised of ABS or other suitable material. As can perhaps best be seen in FIG. 9, the cannula hub 125 includes a rearwardly projecting fin 128 and a pair of wings 130 projecting outwardly and rearwardly at 45 degree angles to the fin 128. The cannula hub 125 includes a vertical bore 132 formed therein. As can be seen in FIG. 8, the vertical bore 132 includes an upper section 134 and a lower section 136 of smaller diameter than the upper section 134. A shoulder or step-down 138 is formed at the juncture between the upper and lower bore sections 134, 136. The vertical bore 134 communicates with a horizontal bore 140 comprising a forward bore section 142 and a rearward bore section 144 having a smaller diameter than the forward bore section 142. A shoulder 146 is formed at the juncture between the forward bore section 142 and the rearward bore section 144.

Also shown in FIG. 8 is a non-coring cannula needle 150 comprised of stainless steel. The cannula needle 150 comprises a shaft 151 and a sharpened forward end 152 which is angled with respect to the shaft 151 in the conventional manner to provide the non-coring feature. The shaft 151 further comprises a rearward end 153. A cannula needle sleeve 154 also comprised of stainless steel is bonded around the shaft 151 at the distal end 153 of the cannula needle 150, such as by an adhesive.

Further shown in FIG. 8 is a cannula tubing 156 having a forward end 157 and a rearward end 158. In the disclosed embodiment the cannula tubing 156 is comprised of polyurethane or other suitable material. A cannula tubing collar 160 comprised of ABS plastic or other suitable material is bonded onto the cannula tubing 156 adjacent the forward end 157 thereof. The inner diameter of the cannula tubing 156 corresponds to the outer diameter of the cannula needle sleeve 154, and the outer diameter of the cannula tubing 156 corresponds to the inner diameter of the forward section 142 of the horizontal bore 140 in the cannula hub 125.

Still referring to FIG. 8, a cannula release sleeve 162 is depicted. The cannula release sleeve 162 has a forward end 164 and a rearward end 166 and in the disclosed embodiment is comprised of stainless steel. The inner diameter of the cannula release sleeve 162 is slightly larger than the outer diameter of the cannula tubing collar 160. A cannula release sleeve bushing 168 comprised of ABS plastic is bonded to the inner wall 170 of the cannula release sleeve 162 at its rearward end 166. The inner diameter of the cannula release sleeve bushing 168 corresponds to the outer diameter of the cannula tubing 156 such that when the cannula tubing 156 is placed within the release sleeve bushing 168 a slight interference fit results.

FIG. 10 shows a cannula subassembly 170 comprising the cannula needle 150 with cannula needle sleeve 154, the cannula tubing 156 with cannula tubing collar 160, the cannula release sleeve 162 with cannula release sleeve bushing 168, and the cannula hub 125. To assemble the cannula subassembly 170, the rearward end 153 of the cannula needle 150 is inserted into the forward end 157 of the cannula tubing 156 and advanced until the cannula needle sleeve 154 bonded to the shaft 151 of the cannula needle 150 is snugly received within the forward end 157 of the cannula tubing 156. The rearward end 158 of the cannula tubing 156 is then inserted through the cannula release sleeve 162 from its forward end 164 until the rearward end 158 of the cannula tubing 156 extends from the rearward end 166 of the cannula release sleeve 162. The fit between the outer diameter of the cannula tubing collar 160 and the inner diameter of the cannula release sleeve 162 is such as will permit the cannula release sleeve 162 to slide freely in an axial direction. The fit between the outer diameter of the cannula tubing 156 and the inner diameter of the cannula release sleeve bushing 168 is such as will provide a slight interference fit between the cannula tubing 156 and cannula release sleeve bushing 168 but will permit the to slide in an axial direction upon exertion of a slight force. With the cannula tubing 156 and cannula release sleeve 162 thus assembled, the rearward end 158 of the cannula tubing 156 is inserted into the forward section 142 of the horizontal bore 140 in the cannula hub 125 and advanced until the distal end 158 of the cannula tubing 156 abuts the shoulder 146.

With the cannula subassembly 170 assembled in this manner, relative axial movement between the cannula tubing 156 and cannula release sleeve 162 is limited by the cannula release sleeve bushing 168 engaging the cannula tubing collar 160. In the disclosed embodiment the dimensions of the various components are configured such that when the cannula release sleeve 162 slides forward until the cannula release sleeve bushing 168 contacts the cannula tubing collar 160, the cannula needle 150 is completely contained within the cannula release sleeve 162.

FIGS. 11A and 11B illustrate a cannula introducer 175 comprising a cannula outer sleeve 178 and a cannula handle 180. The cannula outer sleeve 178 is a tubular member having its upper portion removed at its forward end 182 to form a U-shaped channel 184. The walls of the U-shaped channel 184 circumscribe an arc of slightly greater than 180° such that the width of the opening at the upper end of the channel is narrower than the diameter of the cannula outer sleeve 178. The dimensions of the cannula outer sleeve 178 are such that the cannula subassembly 170 can be slidably received within the U-shaped channel portion 184 at the forward end of the cannula introducer 175 but cannot fit through the opening at the upper end of the U-shaped channel, whereby the cannula subassembly 170 is captured laterally within the cannula introducer 175.

The cannula handle 180 includes inner walls 186 at its forward end 188 which are spaced apart from the cannula outer sleeve 178 to form a recess therebetween. A snap detail 190 is formed at the lower end of the cannula handle to project into the recess. At the upper end of the cannula handle 180 a tongue 192 projects forwardly. The tongue 192 has a longitudinally extending channel 194 formed in its lower face.

FIGS. 12A and 12B show the cannula subassembly 170 mounted to the cannula introducer 175. The fin 128 of the cannula hub 125 is received within the channel 194 in the lower face of the tongue 192 of the cannula handle 180. The cannula release sleeve 162 and cannula tubing 156 reside within the U-shaped channel 184 in the forward end of the cannula outer sleeve 178 with only the forward end 152 of the cannula needle 150 extending beyond the forward end of the cannula introducer 175.

FIG. 13 shows a cannula infusion assembly 200 loaded onto the cannula introducer 175. The cannula infusion subassembly comprises the cannula subassembly 170 having an infusion line 202 inserted into the upper end 134 of the vertical bore 132 in the cannula hub 125. The infusion line 202 is comprised of a thermoplastic elastomer and has an outer diameter which fits snugly within the upper section 134 of the vertical bore 132. The forward end of the infusion line 202 is inserted into the upper bore section 134 and advanced until the forward end of the infusion line engages the shoulder 138. An infusion line restraint pad 204 is mounted to the infusion line and provides strain relief, as will be explained below. The rearward end of the infusion line 202 is connected by a luer adapter 208 to a 3 cc syringe 210 of conventional design.

Figure 14A:
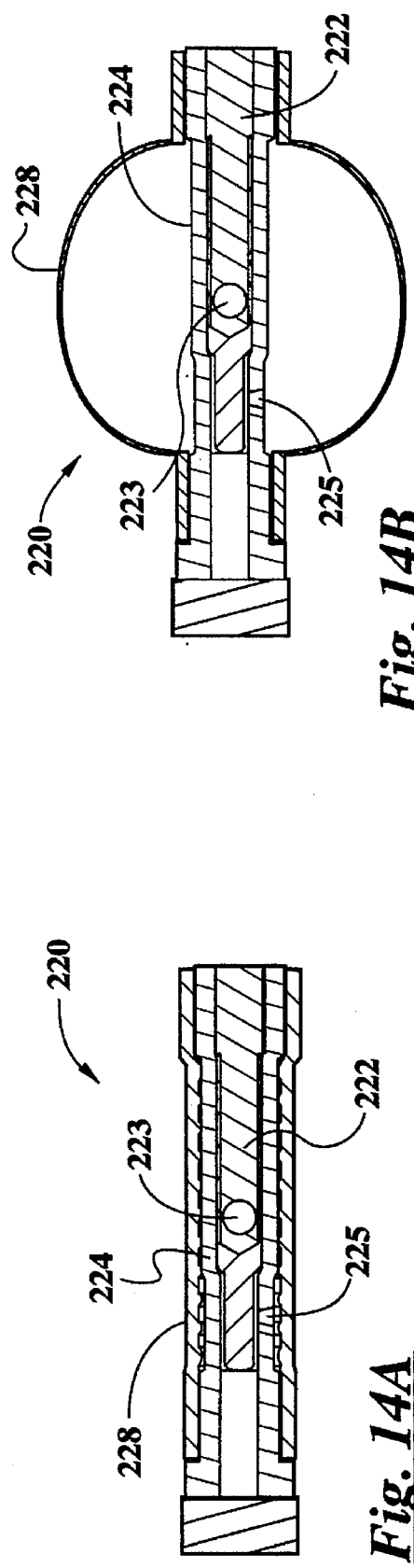
FIG. 14A is a cutaway view of an inflatable prosthesis, in an uninflated state, which is implanted with the apparatus of the disclosed embodiment according to the method of the present invention.

An inflatable prosthesis 220 of a type intended for implantation within periurethral tissues is shown in FIGS. 14A and B. The prosthesis 220 is of a type well known to those skilled in the art and hence will be described herein only briefly. The prosthesis 220 of the disclosed embodiment is sold by the Bard Urological Division, Covington, Ga., USA, under the trademark Genisphere®. The inflatable prosthesis 220 includes a needle guide 222 having a port 223 formed therein. An elastomeric inner housing 224 snugly surrounds the needle guide 222 and includes a hole 225. An elastomeric balloon 228 is disposed around the inner housing 224. To inflate the prosthesis 220, the tip of a catheter or other suitable instrument is inserted into the needle guide 222. Fluid is infused under slight pressure through the catheter and into the needle guide, from where it passes through the port 223. The fluid slightly distends the inner housing 224 and flows into the resulting space between the needle guide 222 and the inner housing 224, finally passing through the hole 225 and causing the outer balloon 228 to inflate. When fluid pressure within the catheter is released, the inner housing 224 returns to its contracted state in snug engagement with the needle guide 222, thereby preventing the return flow of fluid from the balloon and thus serving as a check valve.

The use of the apparatus of the present invention to direct a hypodermic instrument to a predetermined target location without the periurethral tissues is illustrated beginning with FIG. 15. The positioning catheter assembly 40 is assembled to the template assembly 30 by inserting the proximal end 50 of the positioning catheter 42 through the center guide tube 16 of the template 10. The positioning catheter 42 is advanced through the center guide tube 16 until the annular space 63 at the forward end 62 of the catheter collar 48 advances over the distal portion 18 of the center guide tube 16, as shown in FIG. 16A. The positioning catheter assembly 40 is properly positioned with respect to the template assembly 30 when the annular shoulder 64 of the catheter collar 48 abuts the distal end 18 of the center guide tube 16, as shown in FIG. 16B. The positioning catheter assembly 40 is held in position with respect to the template assembly 30 by a friction fit between the first section 60 of the catheter collar 48 and the distal portion 18 of the center guide tube 16. With the positioning catheter assembly 40 thus mounted to the template assembly 30, the proximal end 50 of the positioning catheter 42 projects forward from the front face 11 of the template 10.

With the positioning catheter assembly 40 thus assembled to the template assembly 30, the proximal end 50 of the positioning catheter 42 is advanced through the patient's urethra 250, as shown in FIG. 17, until the proximal end 50 of the positioning catheter 42 resides within the bladder neck 252. The catheter balloon 52 is then inflated in the conventional manner, and the positioning catheter assembly 40 and template assembly 30 are drawn outwardly until the inflated balloon 52a is firmly seated against the bladder neck, as shown in FIG. 18. The four adjustable leg assemblies 32 of the template assembly 30 are then extended by turning the thumb screws 38 to extend the leg assemblies until the pads 36 bear against the patient's abdomen 254. In the disclosed embodiment, the upper pair of leg assemblies 32 bear against the patient's pubic bone, and the lower pair of leg assemblies 32 bears against the pelvic bone. The adjustable leg assemblies 32 thereby exert a constant tension on the positioning catheter 42 and maintain the template 10 at a predetermined distance from the bladder neck 252.

Referring now to FIGS. 19A–C, the two trocar assemblies 110 each comprising a trocar punch 74 and a trocar outer sleeve 90 are introduced through the outer guide sleeves 20 of the template 10. The trocar assemblies 110 are advanced through the periurethral tissues until the trocar outer sleeve adapter 92 engages the reduced rear portion 26 of the center guide sleeve 20. As illustrated more specifically in FIG. 19C, the reduced rear portion 26 of the outer guide sleeve 20 is received within the recess 98 formed between the inner wall 96 of the forward portion 94 of the trocar outer sleeve adapter 92 and the trocar outer sleeve 90. The forward end 93 of the trocar outer sleeve adapter 92 engages the shoulder 28 on the outer guide sleeve 20 and serves as a positive stop to limit the depth of penetration of the trocar punch 74. Because the template 10 is fixed in predetermined spaced relation with respect to the bladder neck 252, the tracts formed by advancing the trocar punches 74 are properly positioned with respect to the bladder neck 252 and urethra 250.

Referring now to FIG. 20, the trocar punches 74 are withdrawn from their respective trocar outer sleeves 90, leaving the trocar outer sleeves 90 in place in the periurethral tissues 256 on either side of the urethra to define a pair of working channels.

FIGS. 21A–D illustrate the loading of the inflatable prostheses 220 onto the cannula infusion assemblies 200. Referring first to FIG. 21A, a prosthesis 220 is inserted into a loading cartridge 114. The interior walls 124 of the loading cartridge 114 center the prosthesis 220 within the cartridge. As shown in FIGS. 21B, the cannula infusion assemblies 200 are loaded onto their respective cannula introducers 175. The cannula needle 150 of the cannula infusion assembly 200 is then inserted into the loading cartridge 114 as illustrated in FIG. 21C until the sharpened forward end 152 of the cannula needle 150 penetrates the core of the prosthesis 220. The cannula infusion assembly 200 and cannula introducer 175 are then withdrawn from the loading cartridge 114, the prosthesis 220 being retained on the end of the cannula needle 150. The second cannula infusion assembly 200 is then loaded with a prosthesis 220 in the same manner.

Referring now to FIG. 22A, the cannula infusion assemblies 200 and cannula introducers 175 are inserted into the rearward end 105 of the trocar outer sleeve adapter 92 and advanced through the periurethral tissues. As shown in FIG. 22B, as the cannula handle 78 advances over the trocar outer sleeve adapter 92, the snap detail 190 of the cannula handle 180 advances past the flange 106 of the trocar outer sleeve adapter 94 to latch the cannula introducer 175 onto the trocar outer sleeve adapter 92. Simultaneously, the wings 130 projecting outwardly and rearwardly from the cannula hub 125 advance past the tabs 29 extending upwardly from the guide sleeve 20 and snap into place behind the tabs, as shown in FIG. 22C. The infusion lines 202 are strain relieved by clamping the infusion line restraint pads 204 to the patient's surgical drape (not shown). At this point both of the cannula infusion assemblies 200 and cannula introducers 175 are inserted into their respective trocar outer sleeve adapters 92.

Referring now to FIG. 23, with the cannula infusion assemblies 200 mechanically engaged within their respective template outer guide sleeves 20, the physician grasps each cannula handle 180 and withdraws the cannula introducers 175. Since the snap detail 190 of each cannula handle 180 is mechanically engaged with the flange 106 of the respective trocar outer sleeve adapter 92, the trocar outer sleeves 90 are withdrawn along with the cannula introducers 175. As the cannula introducers 175 and trocar outer sleeve adapters 92 are withdrawn, the infusion assemblies 200 are retained within their respective guide sleeves 20 by the wings 130 of the cannula hubs 125 confronting the tabs 29 projecting from the guide sleeves 20. Thus when the cannula introducers 175 and trocar outer sleeve adapters 92 are withdrawn, the infusion assemblies 200 remain engaged with the template 10.

When the cannula introducers 175 and trocar outer sleeve adapters 92 have been withdrawn, each prosthesis 220 is partially inflated as shown in FIG. 24 by infusing 1.0 cc of sterile saline from the syringe 210 through the infusion line 202 and hence through the cannula subassembly 170. This partial inflation of the prosthesis 220 tentatively anchors the prosthesis at its implant position within the periurethral tissues 256. The positioning catheter 42 is then deflated and withdrawn from the urethra 250, thereby allowing for a cystoscope 260 to be inserted into the urethra as shown in FIG. 25 to monitor the coaptation effects of the inflatable prostheses 220. The template assembly 30 may also be removed, leaving the cannula subassemblies 170 in place. To remove the template assembly 30, the physician displaces the template 10 downward, disengaging the template from the cannula subassemblies 170 through the openings in the U-shaped outer guide sleeves 20. Then, while the physician cystoscopically monitors the urethra, the prostheses 220 are concurrently inflated with up to 3.0 cc of sterile saline as shown in FIG. 26, causing the urethra 250 to coapt.

At this juncture, the physician may wish to perform urodynamic tests to insure that sufficient pressure is exerted on the urethra to achieve continence. Depending upon the results of the test, inflation of the prostheses 220 may require adjustment to obtain the desired result.

When the physician is satisfied with the extent of pressure exerted by the prostheses, the cannula subassemblies 170 may be withdrawn from the patient. Referring now to FIGS. 27A–B, with the prostheses 220 inflated within the periurethral tissues 256, the physician grasps the cannula release sleeve 162 and holds it in place while withdrawing the cannula hub 125 with the other hand. This relative movement between the cannula release sleeve 162 and the cannula hub 125 accomplishes to purposes. First, since the body of the prosthesis 220 is larger than the diameter of the cannula release sleeve 162, the prosthesis is prevented from moving outwardly as the cannula needle 150 is withdrawn. The cannula needle 150 is thus extracted from the prosthesis 220. Second, the relative movement retracts the cannula needle 150 within the cannula release sleeve 162 so as to protect the user against accidental needle sticks, and the slight friction fit between the cannula release sleeve bushing 168 and the cannula tubing 156 maintains the cannula release sleeve in this extended position. The cannula release sleeve 162 is fully extended with respect to the cannula hub 125 when the cannula release sleeve bushing 168 engages the cannula tubing collar 160, preventing the cannula release sleeve 162 from becoming disengaged from the cannula needle sleeve 154. Withdrawal of the cannula subassembly 170 from the patient completes the procedure.

One feature of the first embodiment of the present invention is the provision of a template assembly 30 which, when firmly mounted to the patient, supports and directs the various instruments for forming the working tracts, implanting the prostheses within the working tracts, and inflating the prostheses so as to coapt the urethra. An advantage of this feature is that a complex procedure involving forming multiple working tracts, implanting multiple prostheses, and inflating the prostheses under cystoscopic monitoring, can be carried out by a single physician. Since the template assembly 30 supports the various instruments, the physician can release the instruments to perform other tasks.

Another feature of the first disclosed embodiment is the provision of a means for properly positioning the inflatable prostheses along the length of the urethra. It has been found that regardless of the length of the patient's urethra, the urethral sphincter is usually positioned at approximately the same position relative to the bladder neck. More particularly, irrespective of the length of the urethra, the urethral sphincter is disposed approximately 1 cm from the bladder neck. Accordingly, by configuring the cannula subassembly 170 such that the inflatable prosthesis 220 extends forward of the front face 11 of the template 10 by a distance 1 cm less than the distance between the front face of the template and the trailing edge of the balloon 52 of the positioning catheter 42, the depth of penetration of the cannula subassembly will be controlled, and the prosthesis will always be properly located along the length of the urethra so as to be properly positioned to coapt the tissues adjacent the sphincter.

A further feature of the first disclosed embodiment is the provision of a means for controlling the depth of penetration of the introducing instruments. Because the trocar punch 74 and cannula subassembly 170 are positively limited by the template 10 from advancing beyond a predetermined depth, the risk of such introducing instruments accidentally overpenetrating and puncturing the bladder or other organ or vessel lying beyond the target location is eliminated.

Still another feature of the first disclosed embodiment is the provision of a means for forming a tract within the periurethral tissues which is parallel to the urethra and in predetermined spaced relation thereto. One advantage of this feature is that, because the catheter locates and fixes the urethra, and because the template defines a pair of axes which are parallel to the axis of the catheter and in predetermined spaced relation thereto, the working channels defined by the template are also parallel to the urethra and in predetermined spaced relation thereto. Further, because the axes of the tracts are spaced apart from the axis of the catheter by the same distance by which the uninflated prosthesis should be spaced from the urethra, the physician using the apparatus of the present invention is always assured that the inflatable prostheses will not be positioned too close or too far from the urethra.

A further advantage of the feature of defining working tracts parallel to the urethra is that since by definition a parallel tracts will never intersect the urethra, it is impossible for the physician accidentally to lacerate or to puncture the urethra during the implantation procedure.

In one aspect the method and apparatus of the present invention provides a means for properly positioning a pair of prostheses in such a manner that the implantation of the first prosthesis does not adversely affect the positioning of the second prosthesis. According to prior art methods, when the first prosthesis is implanted within the periurethral tissues and inflated, the pressure exerted by the prosthesis can displace the urethra from its normal alignment. Then, because the urethra is not in its normal position, the physician can have difficulty in properly locating the second prosthesis with respect to the urethra. According to one aspect of the present invention, however, two steps are taken to minimize this problem. First, the positioning catheter 42 maintains the urethra in its proper alignment throughout the procedure and until both prostheses 220 are inflated. In addition, both prostheses 220 are implanted at their target locations within the periurethral tissues before either prosthesis is inflated. Thus the effects of the urethra being displaced by the inflation of only one prosthesis 220 are substantially eliminated.

FIGS. 28–43 illustrate further embodiments of apparatus and methods for implanting prostheses within periurethral tissues according to the present invention. Since these additional apparatus and methods are in many respects similar to the apparatus and method hereinabove disclosed, these additional apparatus and methods will be disclosed more briefly with emphasis on differences between these further embodiments and the first embodiment hereinabove described.

FIGS. 28–34 illustrate a second embodiment which is similar to the previously described first embodiment in that it operates on the principle of providing a stable reference platform exterior of the patient at a predetermined spaced-apart distance from the bladder neck, whereby the implantation and inflation of a prostheses is performed relative to the stationary reference platform. Referring first to FIGS. 28 and 29, a template 300 is fixedly mounted to a rearward end of an obturator sleeve 302. A conventional Foley catheter 303 having a balloon 304 formed at its forward end has a portion disposed within the obturator sleeve 302. Teeth 305 are formed along one edge of the obturator sleeve 302.

The template 300 includes a pair of guide sleeves 306 extending through the template in a direction parallel to the obturator sleeve 302 and outwardly and downwardly spaced therefrom. Upwardly extending tabs 307 are formed on the lateral edges of the template 300. The tabs 307 each have a beveled outer surface 308 and a forward edge 309.

A tensioning collar 310 is slidably disposed on the obturator sleeve 302. The tensioning collar 310 comprises guide sleeves 312 formed therethrough in coaxial alignment with the guide sleeves 306 in the template 300. A detent 314 formed at the lower end of a cantilevered arm 316 of the tensioning collar 310 engages the teeth 305 formed on the obturator sleeve 302 to lock the tensioning collar with respect to the obturator sleeve. The tensioning collar 310 may be unlocked for sliding movement along the obturator sleeve 302 by squeezing surfaces 318, 320 of the tensioning collar to disengage the detent 314 from the teeth 305. When the tensioning collar has been moved to a desired location, releasing pressure on the surfaces 318, 320 of the tensioning collar 310 will permit the arm 316 to return to its normal position, bringing the detent 314 once again into engagement with the teeth 305 on the edge of the obturator sleeve 302.

Referring now to FIGS. 30 and 31, the tensioning collar 310 is advanced against the introitus 324 of the patient by squeezing the surfaces 318, 320 of the tensioning collar and moving the tensioning collar axially along the obturator sleeve 302. When pressure on the surfaces 318, 320 of the tensioning collar 310 is relaxed, the detent 314 re-engages the teeth 305 of the obturator sleeve 302 to lock the tensioning collar 310 in position.

As will be appreciated, advancing the tensioning collar 310 against the introitus 324 of the patient and locking the tensioning collar on the obturator sleeve 302 exerts a tension on the catheter 303 and draws the balloon 304 into snug engagement with the bladder neck 326 of the patient. The tensioning collar 310 thus serves the same function as the adjustable leg assemblies 32 of the template 10 of the first embodiment. Similarly, because the template 300 is fixed on the obturator sleeve 302 at a predetermined distance from the balloon 304 of the catheter 303, the template 300 provides a fixed reference platform exterior of the patient at a predetermined location with respect to the patient's bladder neck, in the same manner as the template 10 of the first embodiment hereinabove described.

Referring now to FIG. 32, a trocar punch 330 has a trocar punch hub 332 affixed at its rearward end. A trocar sleeve 334 is dimensioned to receive the trocar punch 330 therewithin. A longitudinal slot 335 is formed in the upper surface of the trocar sleeve 334, and a trocar sleeve hub 336 is affixed at the rearward end of the trocar sleeve. The trocar sleeve hub 336 has a locking flange 338 formed at its forward end. Compressing the surfaces 339, 340 of the trocar sleeve hub 336 causes the flange 338 to pivot outward. The inner surface 342 of the locking flange 338 is beveled.

To introduce the trocar punch 330 into the periurethral tissues of the patient, the punch is positioned within the trocar sleeve 334 with the forward end of the trocar punch hub 332 confronting the rearward end of the trocar sleeve hub 336. The trocar punch 330 and sleeve 334 are then advanced together through one of the pair of guide sleeves 306 extending through the template 300 and then through a corresponding one of the guide sleeves 312 formed in the tensioning collar 310. As the trocar punch 330 and sleeve 334 are advanced, the inner surface 342 of the locking flange 338 of the trocar sleeve hub 336 confronts the beveled outer surface 308 of the tab 307 on the template 300. The locking flange 338 is thus biased outward to clear the tab 307. As the trocar sleeve hub 336 continues to advance against the template 300, the locking flange 338 clears the forward edge 309 of the tab 307 of the template 300 and snaps inward, locking the trocar sleeve hub 336 to the template 300, as shown on the left side of FIG. 32. Then, as shown on the right side of FIG. 32, the trocar punch 330 is withdrawn, leaving the trocar sleeve 334 in position by way of the trocar sleeve hub 336 being in locking engagement with the template 300. With the trocar punch 330 withdrawn from the trocar sleeve 334, a working channel is thus provided into the periurethral tissues of the patient.

Referring now to FIGS. 33 and 34, an implant carrying subassembly 350 includes a hub 352 having a fin 353 formed thereon. The implant carrying subassembly 350 further includes a sleeve 354 and a non-coring needle 356. An inflatable prosthesis 220 is mounted on the forward end of the non-coring needle 356. An infusion supply line 358 is in fluid communication with the needle 356 by means of a suitable passage formed in the hub 352 for providing a source of saline solution for inflating the prosthesis 220 on the forward end of the needle. The implant carrying subassembly 350 is advanced through a trocar sleeve 334 with the fin 353 of the implant carrying subassembly hub 352 entering the rearward end of the longitudinal slot 335 of the trocar sleeve 334. The implant carrying subassembly 350 is advanced until the fin 353 of the hub 352 abuts the rearward edge of the template 300. In this position, the implant 220 is disposed within the forward end of the trocar sleeve 334 within the periurethral tissues of the patient.

The next step is to withdraw the trocar sleeve 334 to expose the implant 220 within the periurethral tissues of the patient. By squeezing the surfaces 339, 340 of the trocar sleeve hub 336, the locking flange 338 is pivoted outward to clear the tab 307 of the template 300. The trocar sleeve hub 336 is then pulled rearward, withdrawing the trocar sleeve 334 from the guide bores of the tensioning collar 310 and template 300, as shown on the right side of FIG. 33. As the trocar sleeve 334 is withdrawn, the longitudinal slot 335 formed in the upper surface of the trocar sleeve 334 clears the upstanding fin 353 of the implant carrying subassembly hub 352. The implant carrying subassembly 350 thereby remains in place, with the inflatable prostheses 220 now exposed within the periurethral tissues of the patient. The prostheses 220 is then inflated in the manner hereinabove described with respect to the first embodiment, and the apparatus is then removed from the patient leaving the inflated prostheses implanted.

Both the first and second embodiments hereinabove described operate on the general principle of providing a fixed reference platform exterior of the patient at a predetermined distance from the patient's bladder neck, with the implantation procedure carried out in predetermined relation to the fixed reference platform. While this approach is usually satisfactory, there may be circumstances under which some variation from the fixed, predetermined implant location would be desirable. For example, anatomical irregularities may mandate that the optimal position for the inflatable prostheses is at a location other than 1 cm from the bladder neck. On other occasions, anatomical irregularities may necessitate the positioning of one prosthesis at a depth different from the other prosthesis. FIGS. 35–43 illustrate a third embodiment of an apparatus and method for implanting prostheses within periurethral tissues which permits the physician to exert control over the depth at which the prostheses are positioned.

Referring first to FIGS. 35 and 36, a template 400 comprises an elongated shelf 402 having a housing 404 formed at its forward end. The housing 404 includes a central guide bore 406. Spaced outward and downward from the center guide bore 406 is an opposed pair of outer guide sleeves 408. At the rearward end of the housing 404 a plurality of windows 410 are formed, one in register with each of the central guide bore 406 and outer guide sleeves 408.

Formed on either side of the housing 404 are cantilevered latch arms 414. Each of the latch arms 414 comprises a detent 416 formed on the inner rearward portion thereof. Each latch arm 414 further comprises a pair of surfaces 418, 420 which, when squeezed together, cause the detent 416 to be pivoted outward.

A conventional Foley catheter 424 has a balloon 426 formed at its forward end. A portion of the shaft of the catheter 424 is fixedly disposed within an obturator sleeve 428. The obturator sleeve 428 has on its upper surface an axially spaced series of markings 430 which are serially numbered. The obturator sleeve 428 is slidably disposed within the central guide bore 406 in the housing 404 of the template 400.

Referring now to FIG. 36, the lower surface of the obturator sleeve 428 has a series of teeth 430 formed thereon. A lower latch arm 432 has a detent 434 formed at an upper rearward edge thereof to engage the teeth 430 on the obturator sleeve 428. The template 400 includes a pair of surfaces 436, 438 which, when squeezed, cause the lower latch arm 432 to pivot so as to disengage the detent 434 from the teeth 430 on the obturator sleeve 428.

Referring now to FIGS. 37 and 38, the template 400 is advanced axially over the obturator sleeve 428 to bring the forward end of the template 400 into engagement with the introitus 440 of the patient. Axial movement of the template 400 over the obturator sleeve 428 is accomplished by pressing the opposed surfaces 436, 438 beneath the housing 404 to cause the lower latch arm 432 to pivot and disengage the detent 434 from the teeth 430 on the obturator sleeve. With the detent 434 disengaged, the template 400 is moved forward to the desired location. When pressure on the surfaces 436, 438 of the template 400 is released, the lower latch arm 432 returns to its normal position, bringing the detent 434 into engagement with the teeth 430 on the lower surface of the obturator sleeve 428, thereby locking the template 400 in position. As can be seen in FIG. 37, when the template 400 has been advanced, one of the markings 430 of the obturator sleeve 428 will appear in the window 410 overlying the central guide bore 406 of the housing 404. In FIG. 37, the marking indicated by the numeral "1" is aligned with the window 410.

FIGS. 39 and 40 illustrate the introduction of a trocar punch 450 into the periurethral tissues of the patient. Each trocar punch 450 has a handle 452 attached to its rearward end. The trocar punch 450 is disposed within a trocar sleeve 454 which has a trocar sleeve hub 456 attached at its rearward end. The exterior lateral edges of each trocar sleeve 454 have a plurality of teeth 458 formed thereon. In addition, each trocar sleeve 454 carries a plurality of axially spaced markings 460 corresponding to the markings 430 on the obturator sleeve 428.

The trocar sleeve hub 456 includes a trocar sleeve hub latch 464. The latch 464 has a flange 466 formed at the free end thereof. Squeezing the surfaces 470, 472 of the trocar sleeve hub 456 pivots the latch 464 and displaces the flange 466 outward. The trocar sleeve hub 456 further comprises a rear face 474.

To introduce the trocar punches 450 into the periurethral tissues of the patient, the trocar punch 450 is first assembled into a corresponding trocar sleeve 454 and advanced until the handle 452 of the trocar punch 450 abuts the rearward end of the trocar sleeve hub 456. The assembled trocar punch 450 and sleeve 454 are then advanced into the rearward end of an outer guide sleeve 408. The trocar punch 450 and sleeve 454 are advanced until a marking 460 corresponding to the obturator sleeve marking 430 which appears within the window 410 overlying the central guide bore lies within the window 410 overlying the corresponding outer guide sleeve 408. Axial movement of the trocar sleeve 454 within the outer guide sleeve 408 can be facilitated by squeezing the opposed surfaces 418, 420 of the corresponding lateral latch arm 414 to disengage the detent 416 from the teeth 458 on the lateral edge of the trocar sleeve 454. When the trocar sleeve 454 has been advanced to the desired location, pressure is released from the surfaces 418, 420 of the latch arm 414, whereupon the latch arm returns to its normal position and brings the detent 416 into engagement with the teeth 458 on the lateral edge of the trocar sleeve 454 to lock the trocar sleeve with respect to the template 400. When the trocar sleeve 454 is positioned in the desired location, the trocar punch 450 is withdrawn by squeezing the surfaces 470, 472 on the trocar sleeve hub latch 464, thereby bringing the flange 466 clear of the hub 452 of the trocar punch 450. The trocar punch 450 can now be withdrawn, leaving the trocar sleeve 454 in position to provide a working channel into the periurethral tissues of the patient.

Referring now to FIG. 41, an implant carrying subassembly 480 is introduced into each of the trocar sleeves 454. Each implant carrying subassembly 480 includes a hub 482 having a series of circumferential teeth 484 formed around its forward periphery. The implant carrying subassembly 480 further comprises an elongated sleeve 486 housing a non-coring needle 488. An inflatable prostheses 220 is mounted on the forward end of the needle 488. A supply tubing 490 is in communication with the needle 488 by way of a suitable passageway in the hub 482 for providing a source of saline solution for inflating the prostheses 220 on the forward end of the needle 488.

The implant carrying subassemblies are advanced within their respective trocar sleeves 454 until the forward end 492 of the hub 482 confronts the rear surface of the latch arm 464 of the trocar sleeve hub 456, as can perhaps best be seen in FIG. 42A. In this position, serrations 494 on the upper surface of the shelf 402 of the template 400 engage the circumferential teeth 484 formed on the forward periphery of the hub 482 to restrain the implant carrying subassembly 480 against axial movement.

With the implant carrying subassemblies 480 locked in place, the prostheses 220 mounted at the forward end of the implant carrying subassemblies 480 are located within the forward ends of the trocar sleeves 454. Before the implants 220 can be inflated, it is necessary to retract the trocar sleeves 454 to expose the implants 220 within the periurethral tissues of the patient. As will be recalled, the step of retracting the trocar sleeve while maintaining the implant carrying subassembly in position was accomplished in the previous two embodiments by means of a longitudinal slot formed in the upper portion of each trocar sleeve, which permitted the trocar sleeve to be withdrawn around the implant carrying subassembly. However, the third embodiment employs an arrangement which permits the trocar sleeves 454 to be retracted to expose the prostheses 220 without having to provide slots in the trocar sleeves. As shown in FIG. 42A, the forward end 492 of the hub 482 of the implant carrying subassembly 480 is disposed against the rear surface of the latch arm 464 of the trocar sleeve hub 456. In this position, the forward surface of the implant carrying subassembly hub 482 is spaced apart from the rear face 474 of the trocar sleeve hub 456 by a distance d. By squeezing the surfaces 470, 472 of the trocar sleeve hub 456, the latch arm 464 is pivoted outward to clear the implant carrying subassembly hub 482. The trocar sleeve 454 can now be withdrawn by the distance d until the rear face of the trocar sleeve hub confronts the forward surface of the implant carrying subassembly hub 482, as seen in FIG. 42B. Retracting the trocar sleeve 454 by the distance d causes the forward end of the trocar sleeve to be retracted by the distance d, which substantially corresponds to the length of the inflatable prostheses 220. Thus the trocar sleeve 454 is retracted by a distance sufficient to expose the inflatable prostheses 220 without having to completely remove the trocar sleeve from the template 400. The implant 220 can now be inflated as hereinabove described, and the template 400, trocar sleeves 454, and implant carrying subassemblies 480 are then withdrawn to complete the procedure, leaving the inflated implant in the periurethral tissues.

FIG. 43 illustrates the use of the template 400 in a patient having a longer urethra such that the distance between the balloon 426 of the catheter 424 and the template 400 is greater than that shown in FIGS. 37 and 38. With the template 400 snugged up against the introitus, it will be noted that the marking 430 on the obturator sleeve 428 indicated with the number "4" falls within the window 410 overlying the central guide bore 406. Thus to implant the inflatable prostheses 220 in the conventional position with respect to the bladder neck, the trocar punch 450 and sleeve 454 are advanced until the mark 460 indicated with the number "4" on the trocar sleeve lies within its corresponding window in the housing 404 of the template 400.

Using FIG. 43 as an example, if anatomical considerations require that one of the prostheses 220 be located further from the bladder neck and closer to the surface, then the physician would advance the trocar sleeve 454 only until the marking 460 numbered "3" or "2" fell within the corresponding window 410. Conversely, if it were desired to position the implant 220 closer to the bladder neck, then the physician would advance the trocar sleeve 454 until the marking 460 identified with the number "5" or "6" fell within the window 410. It will be appreciated that, using this method, one or both of the implants 220 can be positioned deeper or shallower than the normal position, or that one implant can be positioned deeper while the other implant is positioned shallower with respect to normal.

It will be appreciated that the third embodiment just described operates in broad principle similar to the first two embodiments previously described, in that a reference plane exterior of the patient is first defined, and then subsequent implantation procedures are carried out with respect to the defined fixed plane. However, while the reference plane in the first two embodiments is defined by a surface of a template, the reference plane in the third embodiment is defined by the location where a landmark on the template 400 intersects a marking on the obturator sleeve. Also, unlike the first two embodiments, the reference plane defined by the third embodiment is not always located at a predetermined distance from the patient's bladder neck, but may lie closer to or more distant from the bladder neck depending upon the patient's anatomy. Thus while the template 400 still defines a fixed reference plane exterior of the patient, that plane is not always in a predetermined relation to the patient's bladder neck.

While the indicia on the obturator sleeve 428 and the indicia on the trocar sleeves 454 are identified by numbers associated therewith, it will be appreciated that other forms of identifying corresponding indicia, such as markings of different colors, markings identified with text, or markings spaced in conventional measurement such as millimeters, may also be used so long as the markings on the obturator sleeve and the markings on the trocar sleeve correspond.

While the arrangement for retracting the trocar sleeve 454 which is depicted in FIGS. 42A and B relies upon positive mechanical stops to ensure that the trocar sleeve is retracted by the correct distance d, it will be appreciated that other methods of demarcating the distance d can be employed. For example, a series of colored bands can be placed on the trocar sleeve with the color sequence repeating every distance d. If a particular landmark such as the rearward edge of the housing intersects a mark of a particular color, the physician simply retracts the trocar sleeve until the next mark of that color intersects the landmark, and the trocar sleeve will have been retracted by the proper distance d.

As will be noted, each of the templates 10, 300, and 400 of the foregoing three disclosed embodiments are shaped differently. It will thus be appreciated that the template can be of any suitable shape so long as the central guide bores and the outer guide sleeves are in predetermined relation to direct the trocars and implant carrier subassemblies properly with respect to the patient's urethra. In particular, it will be appreciated that the forward portion of the template may be curved if desired to provide a mating surface more closely contoured to the patient's anatomy.

The preferred embodiments have been disclosed with respect to templates 10, 300, 400 which define a pair of axes which are parallel to the axis defined by the catheter shaft. Consequently, the templates define a pair of working channels which are parallel to the urethra. However, it will be appreciated that suitable results may also be obtained by a template which defines working channels which terminate at the predetermined target location but which are not parallel to the urethra. By limiting the depth of penetration along a nonparallel path, the template can still ensure that the hypodermic instrument reaches the target location within the periurethral tissues without puncturing the urethra or bladder neck.

It will also be appreciated that the template apparatus of the present invention may be used for purposes other than implanting inflatable prostheses. For example, the template could be used for directing the tip of a hypodermic needle along a line and to a depth corresponding to a target location within the periurethral tissues. A hypodermic needle thus directed could be used, for example, to inject polymers, biopolymers, or the like directly into the periurethral tissues to increase the localized tissue volume in the vicinity of the urethral sphincter. Other purposes for this apparatus will be readily appreciated those skilled in the art.

Finally, it will be understood that the preferred embodiment has been disclosed by way of example, and that other modifications may occur to those skilled in the art without departing from the scope and spirit of the appended claims.

What is claimed is:

1. An apparatus for guiding a tool along a path in predetermined relation with respect to the urethra of a patient, comprising:
   catheter means dimensioned to be inserted into the urethra of a patient for placing said urethra in predetermined alignment;
   template means operatively associated with said catheter means;
   guide means operatively associated with said template means for directing a tool along a path in predetermined relation to said predetermined alignment; and
   standoff means operatively associated with one of said catheter means or said template means for bearing against the abdomen of said patient so as to exert a tension on said catheter means,
   whereby said guide means is operative to direct said tool along said path in predetermined relation with respect to said urethra of said patient.

2. The apparatus of claim 1, wherein said standoff means comprises a tensioning collar operatively associated with said catheter means, said tensioning collar being slidable on said catheter means, and said tensioning collar comprising locking means for selectively locking said tensioning collar with respect to said catheter means, said tensioning collar being slidable on said catheter means to a location bearing against the introitus of said patient and then lockable with respect to said catheter means so as to exert a tension on said catheter means.

3. An apparatus for guiding a tool along a path in predetermined relation with respect to the urethra of a patient, comprising:
   catheter means dimensioned to be inserted into the urethra of a patient for placing said urethra in predetermined alignment;
   template means operatively associated with said catheter means;
   guide means operatively associated with said template means for directing a tool along a path in predetermined relation to said predetermined alignment; and
   means operatively associated with one of said catheter means or said template means for defining a fixed reference plane exterior of said patient such that a tool directed along said path in predetermined relation with respect to said urethra of said patient can be directed to a predetermined depth within the periurethral tissues of said patient by positioning said tool with respect to said fixed reference plane,
   whereby said guide means is operative to direct said tool along said path in predetermined relation with respect to said urethra of said patient.

4. The apparatus of claim 3, wherein said means for defining a fixed reference plane exterior of said patient comprises a surface of said template.

5. The apparatus of claim 3, wherein said means for defining a fixed reference plane exterior of said patient comprises a marking on said catheter means.

6. The apparatus of claim 5, further comprising:
   a punch dimensioned to be received through said guide means so as to be directed along said path in predetermined relation to said predetermined alignment such that when said catheter is inserted into the urethra of said patient and said punch is inserted through said guide means, said punch penetrates the periurethral tissues of said patient; and
   a punch outer sleeve dimensioned to be received through said guide means along with said punch such that when said catheter is inserted into the urethra of said patient and said punch is inserted into the periurethral tissues of said patient, said punch outer sleeve is also inserted into the periurethral tissues of said patient, and such that said punch can be withdrawn, leaving said punch outer sleeve disposed within said periurethral tissues of said patient so as to define a working channel therethrough, said punch further comprising a marking positioned thereon such that when said marking on said punch outer sleeve is correspondingly aligned with said marking on said catheter means, said punch outer sleeve is inserted into the periurethral tissues of said patient to a predetermined depth.

7. The apparatus of claim 6, further comprising a plurality of markings on said punch outer sleeve, whereby a physician can insert said punch outer sleeve to a depth other than said predetermined depth by aligning one of said plurality of markings on said punch outer sleeve other than said marking corresponding to said marking on said catheter means.

8. An apparatus for guiding a tool along a path in predetermined relation with respect to the urethra of a patient, comprising:

catheter means dimensioned to be inserted into the urethra of a patient for placing said urethra in predetermined alignment;

template means operatively associated with said catheter means; and guide means operatively associated with said template means for directing a tool along a path in predetermined relation to said predetermined alignment, whereby said guide means is operative to direct said tool along said path in predetermined relation with respect to said urethra of said patient.

9. The apparatus of claim 8, wherein said template means comprises first and second channels defined therethrough, said catheter means being received within said first channel to operatively associate said template with said catheter means, and said guide means comprising said second channel defined within said template such that a tool inserted through said second channel will be directed along a path in predetermined relation to said predetermined alignment of said urethra.

10. The apparatus of claim 9, wherein said first and second channels defined in said template comprise parallel channels, whereby said path along which a tool is directed is parallel to said predetermined alignment of said urethra.

11. The apparatus of claim 8, further comprising a punch dimensioned to be received through said guide means so as to be directed along said path in predetermined relation to said predetermined alignment such that when said catheter is inserted into the urethra of said patient and said punch is inserted through said guide means, said punch penetrates the periurethral tissues of said patient.

12. The apparatus of claim 11, further comprising a punch outer sleeve dimensioned to be received through said guide means along with said punch such that when said catheter is inserted into the urethra of said patient and said punch is inserted into the periurethral tissues of said patient, said punch outer sleeve is also inserted into the periurethral tissues of said patient, and such that said punch can be withdrawn, leaving said punch outer sleeve disposed within said periurethral tissues of said patient so as to define a working channel therethrough.

13. The apparatus of claim 8, further comprising an instrument for implanting and inflating an inflatable prosthesis, said instrument being operatively associated with said guide means so as to be directed by said guide means along said path in predetermined relation with respect to said urethra of said patient, whereby said instrument is operative to cause an inflatable prosthesis to be implanted and inflated at a location along said path.

14. The apparatus of claim 13, wherein said instrument comprises a means for selectively engaging said template so as to be retained in engagement therewith.

15. The apparatus of claim 8, wherein said template means further comprises a plurality of legs associated therewith for bearing against the abdomen of said patient so as to exert a tension on said catheter means.

16. The apparatus of claim 15, wherein said plurality of legs are selectively extendible.

17. The apparatus of claim 8, wherein said guide means directs said tool along a path which is parallel to said predetermined alignment, whereby a tool directed by said guide means will not lacerate or puncture said urethra.

18. An apparatus for guiding a tool to a predetermined depth with respect to the bladder neck of a patient, comprising:

a catheter having an elongated shaft and being dimensioned to be inserted into the urethra of a patient, said catheter comprising engagement means disposed thereon operative upon said engagement means being introduced into the bladder of said patient for engaging the bladder neck of said patient;

a template operatively associated with said shaft of said catheter at a location in predetermined spaced apart relation to said engagement means of said catheter, whereby when said engagement means engages said bladder neck of said patient said template is located in predetermined location with respect to said bladder neck;

guide means operatively associated with said template for directing a tool along a predetermined path; and stop means operatively associated with said guide means for limiting the extent of tool travel along said predetermined path, whereby when a tool is directed along said predetermined path and advanced until limited by said stop means, said tool is guided to a predetermined depth with respect to said bladder neck of said patient.

19. The apparatus of claim 18, wherein said template comprises first and second channels defined therethrough, wherein said template is operatively associated with said catheter by said catheter being received through said first channel, and wherein said guide means comprises said second channel defined through said template such that a tool inserted through said second channel will be directed along said predetermined path.

20. The apparatus of claim 19, wherein said stop means comprises a collar circumferentially mounted to said catheter at a location on said elongated shaft of said catheter such that when said catheter is inserted through said first channel and advanced until said collar engages said template, said template is located in said predetermined location with respect to said bladder neck.

21. The apparatus of claim 20, wherein said collar defines an annular space between said collar and said shaft of said catheter, wherein said template comprises a sleeve portion, and wherein said collar engages said template by said sleeve portion being snugly received within said annular space so as to form an interference fit with said collar and said catheter shaft.

22. An apparatus for guiding a tool along a predetermined path with respect to the urethra of a patient and to a predetermined depth with respect to the bladder neck of said patient, said apparatus comprising:

catheter means dimensioned to be inserted into the urethra of a patient for placing said urethra in predetermined alignment;

bladder neck engagement means disposed on said catheter means and operative upon said engagement means being introduced into the bladder of said patient for engaging the bladder neck of said patient;

template means operatively associated with said catheter means at a predetermined location with respect to said engagement means of said catheter;

guide means operatively associated with said template means for directing a tool along a path in predetermined relation to said predetermined alignment; and stop means operatively associated with said guide means for limiting the extent of tool travel along said predetermined path, whereby said guide means is operative to direct said tool along a path in predetermined relation with respect to said urethra of said patient; and whereby when said tool is directed along said path and advanced until limited by said stop means, said tool is guided to a predetermined depth with respect to said bladder neck of said patient.

23. An apparatus for placing inflatable prostheses within the periurethral tissues of a patient, comprising:
   a template including first, second, and third guide sleeves, said first, second, and third guide sleeves defining first, second, and third axes, said first and second axes being disposed in predetermined relation to said third axis, and said template including first and second stop means operatively associated with said first and second guide sleeves, respectively;
   a catheter for inserting through said third guide sleeve of said template and into the urethra of said patient, said catheter having a forward end and comprising a balloon adjacent said forward end and selectively inflatable when said catheter is inserted into the urethra of said patient for engaging the bladder neck of said patient, and said catheter having catheter stop means operatively associated therewith for engaging said template to locate said template at a location along said catheter in predetermined spaced relation to said balloon, whereby said template is placed in predetermined axial alignment with said urethra of said patient, and whereby said template is placed in predetermined spaced relation from the bladder neck of said patient;
   first working channel means for insertion through said first guide sleeve of said template for forming a first working channel within said periurethral tissues of said template, said first stop means being operative to limit the extent of travel of said first working channel means such that said first working channel is formed to a predetermined depth with respect to said template;
   second working channel means for insertion through said second guide sleeve of said template for forming a second working channel within said periurethral tissues of said template, said second stop means being operative to limit the extent of travel of said second working channel means such that said second working channel is formed to a predetermined depth with respect to said template;
   first cannula means for insertion through said first guide sleeve of said template for introducing a first inflatable prosthesis through said first working channel and selectively operable to inflate said first inflatable prosthesis with a suitable medium, said first cannula means including engagement means for engaging said template so as to limit the depth to which said first inflatable prosthesis is introduced through said first working channel and for selectively releasably attaching said first cannula means to said template; and
   second cannula means for insertion through said second guide sleeve of said template for introducing a second inflatable prosthesis through said second working channel and selectively operable to inflate said second inflatable prosthesis with a suitable medium, said second cannula means including engagement means for engaging said template so as to limit the depth to which said second inflatable prosthesis is introduced through said second working channel and for selectively releasably attaching said second cannula means to said template.

24. The apparatus of claim 23, wherein said first, second, and third axes defined by said first, second, and third guide sleeves are parallel, whereby when said catheter is placed within the urethra of said patient, said template is engaged with said catheter, and said first and second working channel means are inserted through said first and second guide channel means, said first and second working channels formed by said first and second working channel means are parallel to said urethra of said patient.

25. The apparatus of claim 23, wherein said third guide sleeve comprises a rearward end, and wherein said catheter stop means comprises a collar formed on said catheter which engages said rear guide sleeve end to limit the extent to which said catheter can advance through said third guide sleeve.

26. The apparatus of claim 25, wherein said collar defines an annular recess therewithin, said annular recess being configured to snugly receive said rearward end of said third guide sleeve therewithin to couple said catheter to said template.

27. The apparatus of claim 23, wherein said each of said first and second working channel means comprises a trocar outer sleeve and a trocar punch selectively received within said trocar outer sleeve, whereby said trocar punch and said trocar outer sleeve together can be inserted through the respective guide sleeve to penetrate said periurethral tissues of said patient, and said trocar punch thereafter can be removed from said trocar outer sleeve so as to leave said trocar outer sleeve within said periurethral tissues of said patient to form a working channel.

28. The apparatus of claim 27, wherein said trocar outer sleeve further comprises coupling means for selectively coupling said trocar outer sleeve to said template.

29. The apparatus of claim 23, wherein each of said first and second cannula means comprises means for selectively coupling said first and second cannula means to said template.

30. The apparatus of claim 29, wherein said template comprises at least one tab operatively associated with each of said first and second guide sleeves, and wherein said means for selectively coupling each of said first and second cannula means to said template comprises a laterally extending wing formed on each of said first and second cannula means and operative to engage the corresponding tab on the corresponding guide sleeve.

31. The apparatus of claim 30, wherein each of said wings is comprised of a flexible, resilient material and is angled rearwardly such that each of said wings impinges upon a corresponding tab as its corresponding catheter means is inserted into its respective guide sleeve, flexes as said catheter means is advanced further, and then snaps outwardly as said wing clears said tab, whereby withdrawal of said corresponding catheter means is obstructed by said wing confronting said tab.

32. The apparatus of claim 23, wherein said catheter further comprises a rigid sleeve disposed on a portion of said catheter which resides within the urethra of a patient when said catheter is inserted into said patient, whereby said urethra conforms to the shape of said rigid sleeve.

33. The apparatus of claim 23, wherein said first and second guide sleeves define upwardly opening U-shaped channels, whereby when said first and second working channel means have been withdrawn from said template, said first and second cannula means can be disengaged from said template without removing said first and second cannula means from the periurethral tissues of said patient by displacing said template downward, said first and second cannula means thereby passing through the opening of said U-shaped channels and becoming disengaged from said template.

34. The apparatus of claim 23, further comprising a plurality of legs extensibly mounted to said template and extending forward therefrom, whereby when said template is placed in predetermined spaced relation from the bladder neck of said patient, said legs can be extended forward from said template to bear against the abdominal region of said patient to exert a tension against said catheter and thereby stabilize said template in said predetermined spaced relation from the bladder neck of said patient.

* * * * *